United States Patent
Yabuuchi et al.

(10) Patent No.: US 8,637,557 B2
(45) Date of Patent: Jan. 28, 2014

(54) AMINOTHIAZOLE DERIVATIVE

(75) Inventors: Tetsuya Yabuuchi, Tokyo (JP); Yusuke Oka, Tokyo (JP); Shoichi Kuroda, Tokyo (JP); Takahiro Oi, Tokyo (JP); Yoshinori Sekiguchi, Tokyo (JP)

(73) Assignee: Taisho Pharmaceutical Co., Ltd, Tokyo (JP)

( * ) Notice: Subject to any disclaimer, the term of this patent is extended or adjusted under 35 U.S.C. 154(b) by 0 days.

(21) Appl. No.: 13/502,636

(22) PCT Filed: Oct. 4, 2010

(86) PCT No.: PCT/JP2010/067383
§ 371 (c)(1),
(2), (4) Date: Apr. 18, 2012

(87) PCT Pub. No.: WO2011/048936
PCT Pub. Date: Apr. 28, 2011

(65) Prior Publication Data
US 2012/0220767 A1 Aug. 30, 2012

(30) Foreign Application Priority Data
Oct. 19, 2009 (JP) ................................. 2009-240008

(51) Int. Cl.
*A61K 31/427* (2006.01)
*A61K 31/4245* (2006.01)
*C07D 277/20* (2006.01)
*C07D 271/06* (2006.01)

(52) U.S. Cl.
USPC ............ 514/364; 514/365; 548/131; 548/202

(58) Field of Classification Search
USPC ....................... 514/364, 365; 548/131, 202
See application file for complete search history.

(56) References Cited

U.S. PATENT DOCUMENTS

| | | |
|---|---|---|
| 2006/0293366 A1 | 12/2006 | Baltzer et al. |
| 2009/0029998 A1 | 1/2009 | Quattropani et al. |

FOREIGN PATENT DOCUMENTS

| | | |
|---|---|---|
| JP | 2003501420 | 1/2003 |
| JP | 2007517835 | 7/2007 |
| JP | 2007520478 | 7/2007 |
| WO | 0075120 | 12/2000 |
| WO | 03072557 | 9/2003 |
| WO | 2004007491 | 1/2004 |
| WO | 2004096797 | 11/2004 |
| WO | 2004108708 | 12/2004 |
| WO | 2004108709 | 12/2004 |
| WO | 2005021519 | 3/2005 |
| WO | 2005023800 | 3/2005 |
| WO | 2005068444 | 7/2005 |
| WO | 2005105801 | 11/2005 |
| WO | 2006125803 | 11/2006 |
| WO | 2006125805 | 11/2006 |
| WO | 2007082956 | 7/2007 |
| WO | 2008000421 | 1/2008 |
| WO | 2008025821 | 3/2008 |
| WO | 2008027584 | 3/2008 |

OTHER PUBLICATIONS

CAS RN (1070330-78-7) disclosed on Nov. 3, 2008.*
Marone et al., "Targeting phosphoinositide 3-kinase-Moving towards therapy", Biochimica et Biophysica Acta, 1784:159-185 (2008).
Koyasu, "The role of PI3K in immune cells", Nature Immunol., 4(4):313-319 (2003).
Sasaki et al., "Function of PI3Kγ in Thymocyte Development, T cell Activation, and Neutrophil Migration", Science, 287:1040-1046 (2000).
International Search Report for PCT/JP2010067383 dated Nov. 2, 2012.

* cited by examiner

*Primary Examiner* — Yong Chu
(74) *Attorney, Agent, or Firm* — Sughrue Mion, PLLC

(57) ABSTRACT

A compound represented by formula (1) or a pharmaceutically acceptable salt thereof, which has a PI3 kinase γ inhibitory effect and is useful as a prophylactic or therapeutic agent for articular rheumatism, Crohn's disease, irritable colitis, Sjoegren's syndrome, multiple sclerosis, systemic lupus erythematosus, asthma, atopic dermatitis, arteriosclerosis, organ transplant rejection, cancer, retinopathy, psoriasis, arthrosis deformans, age-related macular degeneration, type II diabetes, insulin resistance, obesity, non-alcoholic fatty liver disease (NAFLD), non-alcoholic steatohepatitis (NASH), hyperlipemia, etc.

6 Claims, No Drawings

AMINOTHIAZOLE DERIVATIVE

CROSS REFERENCE TO RELATED APPLICATIONS

This application is a National Stage of International Application No. PCT/JP2010/067383 filed Oct. 4, 2010, claiming priority based on Japanese Patent Application No. 2009-240008 filed Oct. 19, 2009, the contents of all of which are incorporated herein by reference in their entirety.

TECHNICAL FIELD

The present invention relates to a 2-aminothiazole derivative having an inhibitory action on PI 3-kinase (phosphatidylinositol 3-kinase) γ and a pharmaceutical product containing such a derivative as an effective ingredient.

BACKGROUND ART

PI 3-kinase has been reported to play diverse roles, but its main roles include several basic biological processes including cell proliferation by a platelet-derived growth factor or the like, cytoskeleton regulation, glycometabolism by insulin, neurite extension, immune cell involvement (see Non Patent Literature 1).

PI 3-kinase is an enzyme capable of phosphorylating the hydroxy group at the 3 position of the inositol ring constituting inositol phospholipid, and with phosphatidylinositol, phosphatidylinositol 4-phosphate and phosphatidylinositol 4,5-diphosphate as substrates, produces phosphatidylinositol 3-phosphate, phosphatidylinositol 3,4-diphosphate and phosphatidylinositol 3,4,5-triphosphate, respectively. The phospholipid in which the hydroxy group at the 3 position of the inositol ring is phosphorylated by PI 3-kinase serves as the second messenger to activate serine/threonine kinases such as PDK1 and Akt/PKB in the signal transduction pathways via receptor stimulation. Further, PI 3-kinase plays an important role as a controlling factor in membrane transport. PI 3-kinase is classified into three classes, Types I to III, based on the primary structure, the activity regulatory mechanism and substrate specificity. Among the human PI 3Ks family, all PI 3Ks belonging to Class I are composed of a heterodimer comprising a catalytic subunit (molecular weight: about 110 kDa) and a noncatalytic subunit (molecular weight: 50, 55, 85 or 101 kDa) (see Non Patent Literature 2).

PI 3-kinase γ belonging to Class I is expressed only in the hemopoietic system, and the normal expression is found in a gene deficient mouse but a partial suppression of the adaptive immunity in the immune cells is found. More specifically, suppressions, or the like, of the lymphocyte activation and the neutrophilic leukocyte migration (leukocyte chemotaxis) which occur during the immune response are found (see Non Patent Literature 3), suggesting that PI 3-kinase γ is associated with diseases such as rheumatoid arthritis, Crohn's disease, irritable bowel syndrome, Sjoegren's syndrome, multiple sclerosis, systemic lupus erythematosus, asthma, atopic dermatitis, arteriosclerosis, organ transplant rejection, cancer, retinosis, psoriasis, arthrosis deformans, age-related macular degeneration, type II diabetes mellitus, insulin resistance, obesity, fatty liver (NAFLD), non-alcoholic hepatitis (NASH) or hyperlipidemia.

Thus, PI 3-kinase γ inhibitor is considered to be useful to treat or prevent these diseases.

Up to today, the reported PI 3-kinase γ inhibitors include a certain kind of thiazolidinedione derivatives (see Patent Literature 1), pyridopyrimidine-7-one derivatives (see Patent Literature 2), triazolopyridine derivatives (see Patent Literature 3), aminotetrazole derivatives (see Patent Literatures 3 to 6), and 2-aminothiazole derivatives (see Patent Literatures 7 to 15), however, no compound which has the structure of the present invention is disclosed.

CITATION LIST

Patent Literature

Patent Literature 1: WO2004/007491
Patent Literature 2: WO2005/105801
Patent Literature 3: WO2008/025821
Patent Literature 4: WO2004/108709
Patent Literature 5: WO2004/108708
Patent Literature 6: WO2005/023800
Patent Literature 7: WO2003/072557
Patent Literature 8: WO2004/096797
Patent Literature 9: WO2005/021519
Patent Literature 10: WO2005/068444
Patent Literature 11: WO2006/125805
Patent Literature 12: WO2006/125803
Patent Literature 13: WO2007/082956
Patent Literature 14: WO2008/000421
Patent Literature 15: WO2008/027584

Non Patent Literature

Non Patent Literature 1: Biochim Biophys Acta. 2008 January; 1784(1): 159-85.
Non Patent Literature 2: Nat Immunol. 2003 April; 4(4): 313-9.
Non Patent Literature 3: Science. 2000 Feb. 11; 287(5455): 1040-6.

SUMMARY OF INVENTION

Technical Problem

An object of the present invention is to provide the compound which has a PI 3-kinase γ inhibitory action and is useful as a pharmaceutical product.

Solution to Problem

The present inventors conducted extensive research to meet the above object, and found that the novel amino thiazole derivative (hereinafter sometimes referred to as the compound of the present invention) inhibits the enzyme activity of PI 3Kγ, whereby the present invention has been completed.

More specifically, the present invention provides
<1> A compound represented by a formula (1)

[Formula 1]

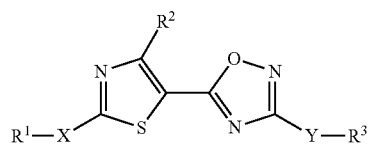

(1)

wherein X represents a formula —NR$^{X1}$—, a formula —C(O) NR$^{X1}$—, a formula —NR$^{X1}$C(O)$_{NR}$$^{X2}$—, a formula —OC(O) NR$^{X1}$— or a formula —SO$_2$NR$^{X1}$—, wherein $R^{X1}$ and $R^{X2}$ are each independently a hydrogen atom or an alkyl group having 1 to 6 carbon atoms;

$R^1$ represents a hydrogen atom, an alkyl group having 1 to 6 carbon atoms, a cycloalkyl group having 3 to 6 carbon atoms or a 5- or 6-membered saturated heterocyclic group, wherein when $R^1$ is an alkyl group having 1 to 6 carbon atoms, the alkyl group may optionally be substituted with 1 to 5 substituents selected from the group consisting of a cycloalkyl group having 3 to 6 carbon atoms, a halogen atom, a cyano group, a hydroxy group, an alkoxy group having 1 to 6 carbon atoms, a formula $-NR^{11}R^{12}$, a formula $-NR^{13}COR^{14}$, a formula $-CO_2R^{15}$, a formula $-CONR^{16}R^{17}$, a formula $-COR^{18}$, a formula $-NR^{19}CONR^{20}R^{21}$, a formula $-SO_2NR^{22}R^{23}$, a formula $-SO_2R^{24}$, a formula $-NR^{25}CO_2R^{26}$, a formula $-OCOR^{27}$ and a 5- or 6-membered heterocyclic group which may optionally be substituted with an alkyl group having 1 to 6 carbon atoms, when $R^1$ is a cycloalkyl group having 3 to 6 carbon atoms, the cycloalkyl group may optionally be substituted with 1 to 5 substituents selected from the group consisting of an alkyl group having 1 to 6 carbon atoms, a hydroxy group, an oxo group, an alkoxy group having 1 to 6 carbon atoms and a formula $-CO_2R^{15}$, when $R^1$ is a 5- or 6-membered saturated heterocyclic group, the saturated heterocyclic group may optionally be substituted with 1 to 5 substituents selected from the group consisting of an alkyl group having 1 to 6 carbon atoms, a hydroxy group, an alkoxy group having 1 to 6 carbon atoms and a formula $-NR^{11}R^{12}$, $R^{11}$, $R^{12}$, $R^{16}$, $R^{17}$, $R^{20}$, $R^{21}$, $R^{22}$ and $R^{23}$ are each independently a hydrogen atom or an alkyl group having 1 to 6 carbon atoms which may optionally be substituted with 1 to 3 substituents selected from a hydroxy group and an alkoxy group having 1 to 6 carbon atoms, or $R^{11}$ and $R^{12}$, $R^{16}$ and $R^{17}$, $R^{20}$ and $R^{21}$, and $R^{22}$ and $R^{23}$, together with the nitrogen atom to which they are bound, may each form a 5- or 6-membered saturated heterocyclic group (wherein the heterocyclic group may optionally be substituted with 1 to 3 substituents selected from the group consisting of a hydroxy group, an alkoxy group having 1 to 6 carbon atoms and an alkoxycarbonyl group having 2 to 7 carbon atoms), and $R^{13}$, $R^{14}$, $R^{15}$, $R^{18}$, $R^{19}$, $R^{24}$, $R^{25}$, $R^{26}$ and $R^{27}$ are each independently a hydrogen atom, or an alkyl group having 1 to 6 carbon atoms which may optionally be substituted with 1 to 3 substituents selected from a hydroxy group and an alkoxy group having 1 to 6 carbon atoms;

$R^2$ represents a hydrogen atom, an alkyl group having 1 to 6 carbon atoms which may optionally be substituted with 1 to 3 halogen atoms, or a halogen atom;

Y represents a single bond, a formula $-CO-$, a formula $-CO_2-$, a formula $-CONR^{Y1}-$, a formula $-NR^{Y1}-$, a formula $-NR^{Y1}CO-$ or a formula $-NR^{Y1}SO_2-$, wherein $R^{Y1}$ is a hydrogen atom or an alkyl group having 1 to 6 carbon atoms; and $R^3$ represents a hydrogen atom, a halogen atom, a cyano group, an alkyl group having 1 to 8 carbon atoms, a cycloalkyl group having 3 to 6 carbon atoms, an alkenyl group having 2 to 6 carbon atoms which may optionally be substituted with a hydroxy group, or a 4- to 6-membered heterocyclic group; and wherein when $R^3$ is an alkyl group having 1 to 8 carbon atoms, the alkyl group may optionally be substituted with 1 to 5 substituents selected from the group consisting of a hydroxy group, a halogen atom, an alkoxy group having 1 to 6 carbon atoms, an alkoxyalkoxy group having 2 to 6 carbon atoms, a cycloalkyl group having 3 to 6 carbon atoms, a cyano group, a phenyl group which may optionally be substituted with 1 to 5 substituents selected from the group consisting of a hydroxy group and a hydroxyalkyl group having 1 to 6 carbon atoms, a 5- or 6-membered heterocyclic group, a formula $-NR^{31}R^{32}$, a formula $-CO_2R^{33}$, a formula $-CONR^{34}R^{35}$, a formula $-OCOR^{36}$, a formula $-SO_2R^{37}$, a formula $-NR^{38}COR^{39}$, a formula $-COR^{40}$, a formula $-SO^2NR^{41}R^{42}$, a formula $-OSO_2R^{43}$, a formula $-NR^{44}CO_2R^{45}$ and a formula $-NR^{46}SO_2R^{47}$, or any one carbon atom of the alkyl group, as the ring-constituting carbon, may form a cycloalkyl ring having 3 to 6 carbon atoms or a 4- to 6-membered saturated heterocyclic ring, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, and $R^{47}$ are each independently a hydrogen atom or an alkyl group having 1 to 6 carbon atoms, and when $R^3$ is a cycloalkyl group having 3 to 6 carbon atoms or a 4- to 6-membered heterocyclic group, the cycloalkyl group and the 4- to 6-membered heterocyclic group may optionally be substituted with 1 to 5 substituents selected from the group consisting of a hydroxy group, an alkoxy group having 1 to 6 carbon atoms, a pyridylmethoxy group, an alkyl group having 1 to 6 carbon atoms, a hydroxyalkyl group having 1 to 6 carbon atoms and an alkoxycarbonyl group having 2 to 7 carbon atoms;

with the proviso that $R^3$ is a halogen atom or a cyano group only when Y is a single bond) or a pharmaceutically acceptable salt thereof.

<2> The compound or a pharmaceutically acceptable salt thereof according to <1>, wherein when X is a formula $-NH-$, $R^1$ is not a hydrogen atom, or when $R^3$ is a group selected from 4- to 6-membered heterocyclic group, $R^3$ is not a thienyl group; with the proviso that N,4-dimethyl-5-[3-(pyridin-3-ylmethyl)-1,2,4-oxadiazol-5-yl]-1,3-thiazol-2-amine, N-ethyl-4-methyl-5-[3-(1-methylimidazol-4-yl)-1,2,4-oxadiazol-5-yl]-1,3-thiazol-2-amine, N-ethyl-4-methyl-5-[3-(pyridin-2-yl)-1,2,4-oxadiazol-5-yl]-1,3-thiazol-2-amine, and N-[5-(3-benzyl-1,2,4-oxadiazol-5-yl)-4-(trifluoromethyl)-1,3-thiazol-2-yl]-$N^2$-[(2S)-2-hydroxy-3,3-dimethylbutanoyl]-L-norvalinamide are excluded.

<3> The compound or a pharmaceutically acceptable salt thereof according to <1>, wherein X represents a formula $-NR^{X1}-$, a formula $-C(O)NR^{X1}-$, a formula or a formula $-OC(O)NR^{X1}-$, wherein $R^{X1}$ and $R^{X2}$ are each independently a hydrogen atom or an alkyl group having 1 to 6 carbon atoms;

$R^1$ is a hydrogen atom, an alkyl group having 1 to 6 carbon atoms, a cycloalkyl group having 3 to 6 carbon atoms which may optionally be substituted with a formula $-CO_2R^{15}$, or a 5- to 6-membered saturated heterocyclic group which may optionally be substituted with a hydroxy group, wherein when $R^1$ is an alkyl group having 1 to 6 carbon atoms, the alkyl group may optionally be substituted with 1 to 5 substituents selected from the group consisting of a hydroxy group, an alkoxy group having 1 to 6 carbon atoms, a formula $-NR^{11}R^{12}$, a formula $-NR^{13}COR^{14}$, a formula $-CO_2R^{15}$, a formula $-CONR^{16}R^{17}$, a formula $-SO^2NR^{22}R^{23}$, a formula $-NR^{25}CO_2R^{26}$, a formula $-OCOR^{27}$ and a 5- or 6-membered heterocyclic group which may optionally be substituted with an alkyl group having 1 to 6 carbon atoms, $R^{11}$, $R^{12}$, $R^{16}$, $R^{17}$, $R^{22}$ and $R^{23}$ are each independently a hydrogen atom or an alkyl group having 1 to 6 carbon atoms which may optionally be substituted with 1 to 3 substituents selected from a hydroxy group and an alkoxy group having 1 to 6 carbon atoms, or $R^{16}$ and $R^{17}$, together with the nitrogen atom to which they are bound, may form a 5- or 6-membered saturated heterocyclic group (wherein the heterocyclic group may optionally be substituted with 1 to 3 substituents selected from the group consisting of a hydroxy group, an alkoxy group having 1 to 6 carbon atoms and an alkoxycarbonyl group having 2 to 7 carbon atoms), and $R^{13}$, $R^{14}$, $R^{15}$, $R^{25}$, $R^{26}$ and $R^{27}$ are each independently a hydrogen atom, or an alkyl group having 1 to 6 carbon atoms which may optionally be substituted with a hydroxy group;

$R^2$ is an alkyl group having 1 to 6 carbon atoms;

Y represents a single bond, a formula —CO—, a formula —CO$_2$— or a formula —CONR$^{Y1}$—, wherein $R^{Y1}$ represents a hydrogen atom, or an alkyl group having 1 to 6 carbon atoms; and $R^3$ is a hydrogen atom, an alkyl group having 1 to 8 carbon atoms, a cycloalkyl group having 3 to 6 carbon atoms, an alkenyl group having 2 to 6 carbon atoms which may optionally be substituted with a hydroxy group, or a 4- to 6-membered heterocyclic group, wherein when $R^3$ is an alkyl group having 1 to 8 carbon atoms, the alkyl group may optionally be substituted with 1 to 5 substituents selected from the group consisting of a hydroxy group, a halogen atom, an alkoxy group having 1 to 6 carbon atoms, an alkoxyalkoxy group having 2 to 6 carbon atoms, a cycloalkyl group having 3 to 6 carbon atoms, a phenyl group which may optionally be substituted with 1 to 5 substituents selected from the group consisting of a hydroxy group and a hydroxyalkyl group having 1 to 6 carbon atoms, a 5- or 6-membered heterocyclic group, a formula —NR$^{31}$R$^{32}$, a formula —CO$_2$R$^{33}$, a formula —CONR$^{34}$R$^{35}$, a formula —OCOR$^{36}$, a formula —SO$_2$R$^{37}$, a formula —NR$^{38}$COR$^{39}$, a formula —COR$^{40}$, a formula —SO$_2$NR$^{41}$R$^{42}$, a formula —OSO$_2$R$^{43}$, a formula —NR$^{44}$CO$_2$R$^{45}$ and a formula —NR$^{46}$SO$_2$R$^{47}$, or any one carbon atom of the alkyl group, as the ring-constituting carbon, may form a cycloalkyl ring having 3 to 6 carbon atoms or a 4- to 6-membered saturated heterocyclic ring, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$ and $R^{47}$ are each independently a hydrogen atom or an alkyl group having 1 to 6 carbon atoms, and when $R^3$ is a cycloalkyl group having 3 to 6 carbon atoms or a 4- to 6-membered heterocyclic group, the cycloalkyl group and the 4- to 6-membered heterocyclic group may optionally be substituted with 1 to 5 substituents selected from the group consisting of a hydroxy group, an alkoxy group having 1 to 6 carbon atoms, a pyridylmethoxy group, an alkyl group having 1 to 6 carbon atoms, a hydroxyalkyl group having 1 to 6 carbon atoms and an alkoxycarbonyl group having 2 to 7 carbon atoms.

<4> The compound or a pharmaceutically acceptable salt thereof according to any one of <1> to <3>, wherein X is a formula —C(O)NH—; and $R^1$ is a hydrogen atom, an alkyl group having 1 to 6 carbon atoms, a cycloalkyl group having 3 to 6 carbon atoms which may optionally be substituted with a formula —CO$_2$R$^{15}$, or a 5- to 6-membered saturated heterocyclic group which may optionally be substituted with a hydroxy group, wherein when $R^1$ is an alkyl group having 1 to 6 carbon atoms, the alkyl group may optionally be substituted with 1 to 5 substituents selected from the group consisting of a hydroxy group, an alkoxy group having 1 to 6 carbon atoms, a formula —NR$^{11}$R$^{12}$, a formula —CO$_2$R$^{15}$, a formula —CONR$^{16}$R$^{17}$, a formula —SO$_2$NR$^{22}$R$^{23}$, a formula —NR$^{25}$CO$_2$R$^{26}$ and a formula —OCOR$^{27}$, $R^{11}$, $R^{12}$, $R^{16}$, $R^{17}$, $R^{22}$ and $R^{23}$ are each independently a hydrogen atom, or an alkyl group having 1 to 6 carbon atoms which may optionally be substituted with 1 to 3 substituents selected from a hydroxy group and an alkoxy group having 1 to 6 carbon atoms, and $R^{15}$, $R^{25}$, $R^{26}$ and $R^{27}$ are each independently a hydrogen atom, or an alkyl group having 1 to 6 carbon atoms which may optionally be substituted with a hydroxy group.

<5> The compound or a pharmaceutically acceptable salt thereof according to any one of <1> to <3>, wherein X is a formula —NHC(O)NH— or a formula —OC(O)NH—.

<6> The compound or a pharmaceutically acceptable salt thereof according to any one of <1> to <3> or <5>, wherein $R^1$ is an alkyl group having 1 to 6 carbon atoms, the alkyl group may optionally be substituted with 1 to 5 substituents selected from the group consisting of a formula —CO$_2$R$^{15}$, a formula —CONR$^{16}$R$^{17}$ and a 5- or 6-membered heterocyclic group which may optionally be substituted with an alkyl group having 1 to 6 carbon atoms, $R^{16}$ and $R^{17}$ are each independently a hydrogen atom or an alkyl group having 1 to 6 carbon atoms which may optionally be substituted with 1 to 3 substituents selected from a hydroxy group and an alkoxy group having 1 to 6 carbon atoms, or $R^{16}$ and $R^{17}$, together with the nitrogen atom to which they are bound, may form a 5- or 6-membered saturated heterocyclic group (wherein the heterocyclic group may optionally be substituted with 1 to 3 substituents selected from the group consisting of a hydroxy group, an alkoxy group having 1 to 6 carbon atoms and an alkoxycarbonyl group having 2 to 7 carbon atoms), and $R^{15}$ represents a hydrogen atom, or an alkyl group having 1 to 6 carbon atoms which may optionally be substituted with a hydroxy group.

<7> The compound or a pharmaceutically acceptable salt thereof according to any one of <1> to <6>, wherein Y is a single bond.

<8> The compound or a pharmaceutically acceptable salt thereof according to any one of <1> to <7>, wherein $R^3$ represents an alkyl group having 1 to 8 carbon atoms, a cycloalkyl group having 3 to 6 carbon atoms, an alkenyl group having 2 to 6 carbon atoms substituted with a hydroxy group, or a 4- to 6-membered heterocyclic group, wherein when $R^3$ is an alkyl group having 1 to 8 carbon atoms, the alkyl group may optionally be substituted with 1 to 5 substituents selected from the group consisting of a hydroxy group, a halogen atom, an alkoxy group having 1 to 6 carbon atoms, a cycloalkyl group having 3 to 6 carbon atoms, a formula —CO$_2$R$^{33}$, a formula —CONR$^{34}$R$^{35}$, a formula —SO$_2$R$^{37}$, a formula —NR$^{38}$COR$^{39}$ and a formula —COR$^{40}$, or any one carbon atom of the alkyl group, as the ring-constituting carbon, may form a cycloalkyl ring having 3 to 6 carbon atoms or a 4- to 6-membered saturated heterocyclic ring, $R^{33}$, $R^{34}$, $R^{35}$, $R^{37}$, $R^{38}$, $R^{39}$ and $R^{40}$ are each independently a hydrogen atom, or an alkyl group having 1 to 6 carbon atoms, and when $R^3$ is a cycloalkyl group having 3 to 6 carbon atoms or a 4- to 6-membered heterocyclic group, the cycloalkyl group having 3 to 6 carbon atoms and the 4- to 6-membered heterocyclic group may optionally be substituted with 1 to 5 substituents selected from the group consisting of a hydroxy group, an alkoxy group having 1 to 6 carbon atoms, an alkyl group having 1 to 6 carbon atoms, a hydroxyalkyl group having 1 to 6 carbon atoms and an alkoxycarbonyl group having 2 to 7 carbon atoms.

<9> The compound or a pharmaceutically acceptable salt thereof according to any one of <1> to <7>, wherein $R^3$ is an alkyl group having 1 to 8 carbon atoms substituted with a hydroxy group, or a 4- to 6-membered heterocyclic group which may optionally be substituted with a hydroxy group.

<10> The compound or a pharmaceutically acceptable salt thereof according to any one of <1> to <7>, wherein R³ is a pyridyl group.

<11> The compound or a pharmaceutically acceptable salt thereof according to any one of <1> to <7>, wherein R³ is a 4- to 6-membered nitrogen-containing saturated heterocyclic group substituted with a hydroxy group.

<12> A prophylactic or therapeutic agent for rheumatoid arthritis, Crohn's disease, irritable bowel syndrome, Sjoegren's syndrome, multiple sclerosis, systemic lupus erythematosus, asthma, atopic dermatitis, arteriosclerosis, organ transplant rejection, cancer, retinosis, psoriasis, arthrosis deformans, age-related macular degeneration, type II diabetes mellitus, insulin resistance, obesity, fatty liver (NAFLD), non-alcoholic hepatitis (NASH) or hyperlipidemia, the agent comprising as an effective ingredient a compound or a pharmaceutically acceptable salt thereof according to any one of <1> to <11>.

Advantageous Effects of Invention

The compound of the present invention has the inhibitory activity on PI 3 Kγ.

DESCRIPTION OF EMBODIMENTS

In the present invention, the alkyl group having 1 to 6 carbon atoms refers to a linear or branched alkyl group having 1 to 6 carbon atoms, and the examples thereof include a methyl group, an ethyl group, a n-propyl group, an isopropyl group, a n-butyl group, an isobutyl group, a tert-butyl group, a sec-butyl group, a n-pentyl group, an isopentyl group, a neopentyl group, a tert-pentyl group, and a n-hexyl group. Similarly, the alkyl group having 1 to 8 carbon atoms refers to a linear or branched alkyl group having 1 to 8 carbon atoms, and the examples thereof include, in addition to the above substituents, a n-heptyl group, and a n-octyl group.

The alkenyl group having 2 to 6 carbon atoms refers to a linear or branched alkenyl group having 2 to 6 carbon atoms, and the examples thereof include a vinyl group, an allyl group, a 1-propenyl group, an isopropenyl group, a 1-butenyl group, a 2-butenyl group, a 3-butenyl group, a 2-methylallyl group, a 2-methylpropenyl group, and a 4-pentenyl group.

The cycloalkyl group having 3 to 6 carbon atoms refers to a cyclopropyl group, a cyclobutyl group, a cyclopentyl group and a cyclohexyl group.

The alkoxy group having 1 to 6 carbon atoms refers to a linear or branched alkoxy group having 1 to 6 carbon atoms, and the examples thereof include a methoxy group, an ethoxy group, a n-propoxy group, an isopropoxy group, a n-butoxy group, an isobutoxy group, a sec-butoxy group, a tert-butoxy group, a n-pentyloxy group, and a n-hexyloxy group.

The alkoxycarbonyl group having 2 to 7 carbon atoms refers to a combined form of a linear or branched alkoxy group having 1 to 6 carbon atoms and a carbonyl group, and the examples thereof include a methoxycarbonyl group, an ethoxycarbonyl group, a n-propoxycarbonyl group, an isopropoxycarbonyl group, a n-butoxycarbonyl group, an isobutoxycarbonyl group, a tert-butoxycarbonyl group, a sec-butoxycarbonyl group, a n-pentyloxycarbonyl group, an isopentyloxycarbonyl group, and a neopentyl oxycarbonyl group.

The alkoxyalkoxy group having 2 to 6 carbon atoms refers to a linear or branched alkoxyalkoxy group having 2 to 6 carbon atoms, and the examples thereof include a 2-methoxyethoxy group, a 2-ethoxyethoxy group, a 2-tert-butoxyethoxy group, a 3-methoxypropoxy group, and a 4-methoxybutoxy group.

The hydroxyalkyl group having 1 to 6 carbon atoms refers to a linear or branched hydroxyalkyl group having 1 to 6 carbon atoms, and the examples thereof include a hydroxymethyl group, a 1-hydroxyethyl group, a 2-hydroxyethyl group, a 3-hydroxypropyl group, a 4-hydroxybutyl group, and a 2-hydroxypropan-2-yl group.

The 5- or 6-membered heterocyclic group refers to a saturated heterocyclic group, an aromatic heterocyclic group or a partially saturated aromatic heterocyclic group, each of which is 5- or 6-membered and contains 1 to 4 hetero atoms selected from an oxygen atom, a nitrogen atom or a sulfur atom in the ring. The saturated heterocyclic group or the partially saturated aromatic heterocyclic group may optionally be substituted with an oxo group. The examples thereof include a tetrahydrofuranyl group, a tetrahydropyranyl group, a morpholinyl group, a morpholino group, a pyrrolidinyl group, 2-oxo-pyrrolidinyl group, a piperidyl group, a piperidino group, a piperazinyl group, a piperazino group, an imidazolyl group, a pyrazolyl group, an oxazolyl group, an isoxazolyl group, an oxadiazolyl group, a thiazolyl group, a triazolyl group, a tetrazolyl group, a pyridyl group, a pyrimidyl group, a pyrazyl group, and a 6-oxo-1,6-dihydropyridyl group. Similarly, the 4- to 6-membered heterocyclic group refers to a 4- to 6-membered saturated heterocyclic group, an aromatic heterocyclic group or a partially saturated aromatic heterocyclic group, each of which is 4- to 6-membered and contains 1 to 4 hetero atoms selected from an oxygen atom, a nitrogen atom or a sulfur atom in the ring. The saturated heterocyclic group or the partially saturated aromatic heterocyclic group may optionally be substituted with an oxo group. The examples thereof include, in addition to the above substituents, an oxetanyl group, and an azetidinyl group.

The 4- to 6-membered nitrogen-containing saturated heterocyclic group refers to a group which contains at least one nitrogen atom in the ring among the above 4- to 6-membered saturated heterocyclic groups, and the examples thereof include an azetidinyl group, a pyrrolidinyl group, a piperidyl group, a piperidino group, a piperazinyl group, a piperazino group, a morpholinyl group, and a morpholino group.

The halogen atom refers to a fluorine atom, a chlorine atom, a bromine atom and an iodine atom.

The examples of the structure defined as the "any one carbon atom of the alkyl group, as the ring-constituting carbon, may form a cycloalkyl ring having 3 to 6 carbon atoms or a 4- to 6-membered saturated heterocyclic ring" include a (3-methyloxetan-3-yl)methyl group and a (1-methylcyclopropyl)methyl group.

Further, the pharmaceutically acceptable salt refers to salts with alkali metals, alkaline earth metals, ammonium, alkyl ammonium, etc., salts with mineral acids or organic acids. The examples of such salts include sodium salts, potassium salts, calcium salts, ammonium salts, aluminium salts, triethylammonium salts, acetates, propionates, butyrates, formic acid salts, trifluoroacetic acid salts, maleates, tartrates, citrates, stearates, succinates, ethylsuccinates, lactobionates, gluconates, glucoheptonates, benzoates, methanesulfonates, ethanesulfonates, 2-hydroxyethanesulfonates, benzenesulfonates, p-toluenesulfonates, lauryl sulfates, malates, aspartates, glutamates, adipates, salts with cysteine, salts with N-acetylcysteine, hydrochlorides, hydrobromates, phosphates, sulfates, hydrogen iodide salts, nicotinates, oxalates, picrates, thiocyanates, undecanoates, salts with acrylic acid polymer, and salts with carboxy vinyl polymer.

The compound of the present invention can contain more than one asymmetric center. Consequently, the compounds described above can exist in the form of optically active substance as well as the racemate thereof, and can further exist in the form of more than one diastereoisomers. Any forms mentioned above are encompassed within the scope of the present invention. Each isomer can be obtained by known methods such as using an optically active starting material or intermediate, optically selective reaction or diastereoselective reaction in the production of the intermediate or the final product, or chromatographic separation in the production of the intermediate or the final product. Further, when the compound of the present invention forms a hydrate or a solvate, they are also encompassed within the scope of the present invention. Equally, the pharmaceutically acceptable salts of the hydrate or the solvate of the compound of the present invention are also encompassed within the scope of the present invention.

The compound of the present invention can be synthesized by, for example, the following production methods. In the general synthesis methods, $R^1$, $R^2$, $R^3$, $R^{Y1}$, X and Y are defined as above, Hal represents a chlorine atom, a bromine atom or an iodine atom, and R represents an alkyl group having 1 to 6 carbon atoms.

General Synthesis Method 1

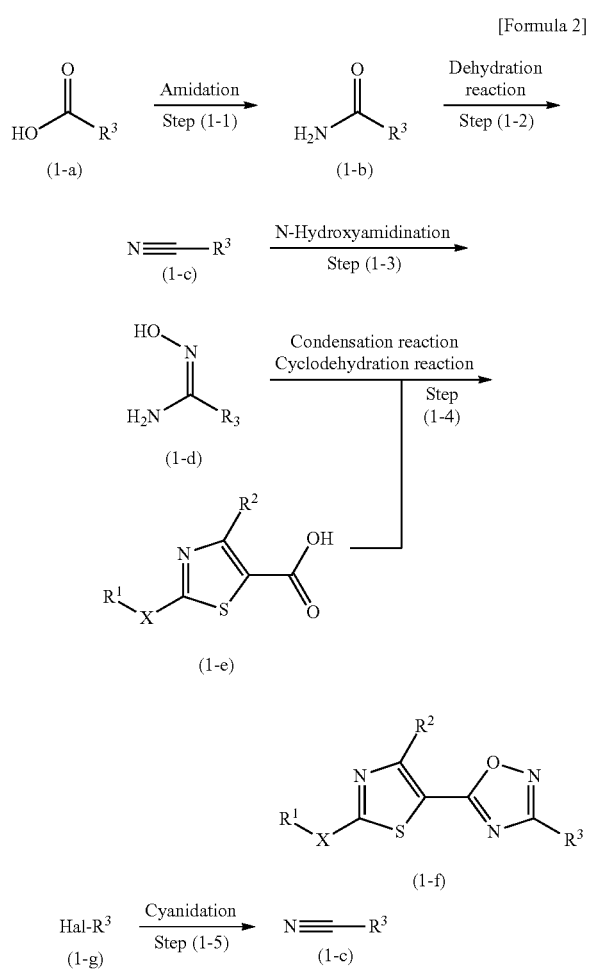

Step (1-1): The compound 1-a may be reacted with ammonium chloride in an ether solvent such as tetrahydrofuran or dioxane, a halogen solvent such as methylene chloride or chloroform, an aromatic hydrocarbon solvent such as toluene or xylene, or an aprotic polar solvent such as N,N-dimethylformamide or N,N-dimethylacetamide, in the presence or absence of a base such as triethylamine or pyridine, and a condensation agent such as dicyclohexylcarbodiimide (DCC), 1-(3-dimethylaminopropyl)-3-ethylcarbodiimide (EDC) hydrochloride or benzotriazol-1-yloxytripyrrolidino phosphonium hexafluorophosphoric acid salt (PyBOP (R)) to produce the compound 1-b. The compound 1-b may also be produced by reacting the compound 1-a with N,N-carbonyldiimidazole (CDI), and further reacting with ammonia.

Step (1-2): The compound 1-b may be reacted in an ether solvent such as tetrahydrofuran or dioxane, a halogen solvent such as methylene chloride or chloroform, an aromatic hydrocarbon solvent such as toluene or xylene, in the presence or absence of a base such as triethylamine or pyridine, with a dehydrating agent such as phosphoryl trichloride, trifluoroacetic anhydride, thionyl chloride, trifluoromethanesulfonic anhydride, diphosphorus pentaoxide, p-toluene sulfonylchloride, cyanuric trichloride, or methoxycarbonylsulfamoyl)triethylammonium hydroxide inner salt (Burgess reagent) to produce the compound 1-c.

Step (1-3): The compound 1-c may be reacted in water, an alcohol solvent such as methanol or ethanol or ether solvent such as tetrahydrofuran or dioxane, with an aqueous solution of hydroxylamine or an aqueous solution of hydroxylamine obtained from hydroxylamine hydrochloride with an inorganic base such as sodium bicarbonate, potassium bicarbonate, sodium carbonate, potassium carbonate, sodium hydroxide, potassium hydroxide or lithium hydroxide, to produce the compound 1-d.

Step (1-4): The compound 1-d and the compound 1-e may be reacted in an ether solvent such as tetrahydrofuran or dioxane, a halogen solvent such as methylene chloride or chloroform, an aromatic hydrocarbon solvent such as toluene or xylene, or an aprotic polar solvent such as N,N-dimethylformamide or N,N-dimethylacetamide, in the presence or absence of a base such as triethylamine or pyridine, with a condensation agent such as dicyclohexylcarbodiimide (DCC), 1-(3-dimethylaminopropyl)-3-ethylcarbodiimide (EDC) hydrochloride or benzotriazol-1-yloxytripyrrolidino phosphonium hexafluorophosphoric acid salt (PyBOP (R)), and, where necessary, with an additive such as 1-hydroxybenzotriazole monohydrate (HOBt), and the reaction mixture may be stirred while heating in the presence or absence of an additive such as molecular sieves to produce the compound 1-f of the present invention.

Step (1-5): The compound 1-c may also be produced by reacting the compound 1-g with sodium cyanide or potassium cyanide in an aprotic polar solvent such as N,N-dimethylformamide, N,N-dimethylacetamide or dimethyl sulfoxide, water, acetonitrile or an alcohol solvent such as methanol or ethanol.

Step (1-6): The compound 1-c may also be produced by reacting the compound 1-h with a dehydrating agent such as phosphoryl trichloride, trifluoroacetic anhydride, thionyl chloride, trifluoromethanesulfonic anhydride, diphosphorus pentaoxide, p-toluene sulfonylchloride, cyanuric trichloride, or (methoxycarbonylsulfamoyl)triethylammonium hydroxide inner salt (Burgess reagent) in an ether solvent such as tetrahydrofuran or dioxane, a halogen solvent such as methylene chloride or chloroform, an aromatic hydrocarbon solvent such as toluene or xylene, in the presence or absence of a base such as triethylamine or pyridine.

Step (1-7) When $R^3$ is a 4- to 6-membered nitrogen-containing saturated heterocyclic group, the compound 1-c may also be produced by reacting the compound 1-i with cyanogen chloride, cyanogen bromide, etc., in an ether solvent such as tetrahydrofuran or dioxane, a halogen solvent such as methylene chloride or chloroform, an aromatic hydrocarbon solvent such as toluene or xylene, or an aprotic polar solvent such as N,N-dimethylformamide or N,N-dimethylacetamide, in the presence or absence of a base such as triethylamine or pyridine.

General Synthesis Method 2

[Formula 3]

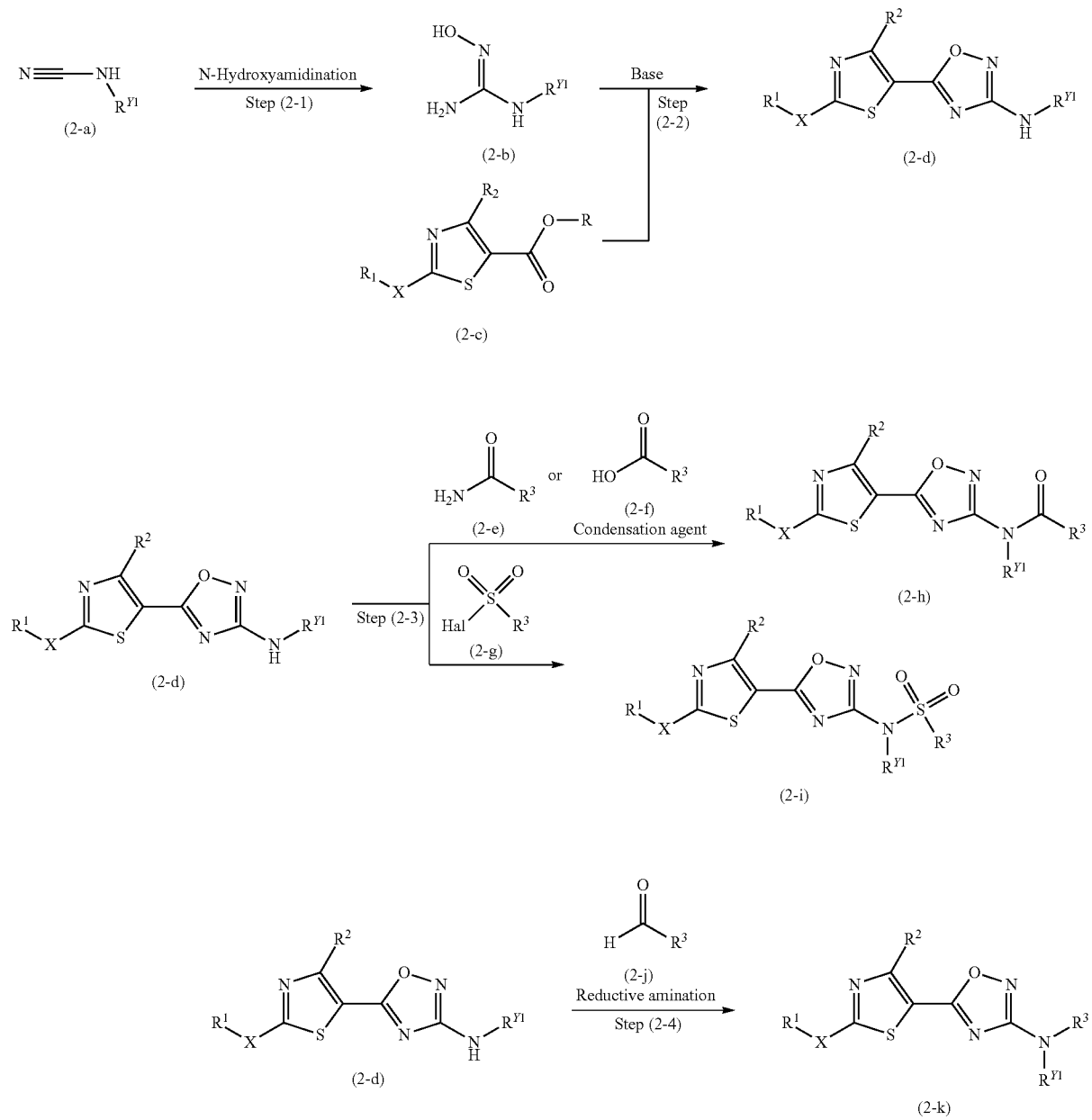

Step (2-1): The compound 2-a may be reacted with an aqueous solution of hydroxylamine or an aqueous solution of hydroxylamine obtained from hydroxylamine hydrochloride with an inorganic base such as sodium bicarbonate, potassium bicarbonate, sodium carbonate, potassium carbonate, sodium hydroxide, potassium hydroxide or lithium hydroxide, in water, an alcohol solvent such as methanol or ethanol or ether solvent such as tetrahydrofuran or dioxane, to produce the compound 2-b.

Step (2-2): The compound 2-b may be reacted with a base such as sodium ethoxide, potassium tert-butoxide, sodium hydride, in an ether solvent such as tetrahydrofuran or dioxane, an alcohol solvent such as methanol or ethanol or an aprotic polar solvent such as N,N-dimethylformamide or N,N-dimethylacetamide, and the compound 2-c may be added to the reaction mixture and heated to produce the compound 2-d of the present invention.

Step (2-3): The compound 2-h of the present invention or the compound 2-i of the present invention may be produced by reacting the compound 2-d with the compound 2-e or the compound 2-g, respectively, in an ether solvent such as tetrahydrofuran or dioxane, a halogen solvent such as methylene chloride or chloroform, an aromatic hydrocarbon solvent such as toluene or xylene, or an aprotic polar solvent such as N,N-dimethylformamide or N,N-dimethylacetamide, in the presence or absence of a base such as triethylamine or pyridine.

The compound 2-d and the compound 2-f may be reacted in an ether solvent such as tetrahydrofuran or dioxane, a halogen solvent such as methylene chloride or chloroform, an aromatic hydrocarbon solvent such as toluene or xylene, or an aprotic polar solvent such as N,N-dimethylformamide or N,N-dimethylacetamide, in the presence or absence of a base such as triethylamine or pyridine, with a condensation agent such as dicyclohexylcarbodiimide (DCC), 1-(3-dimethylaminopropyl)-3-ethylcarbodiimide (EDC) hydrochloride or benzotriazol-1-yloxytripyrrolidino phosphonium hexafluorophosphoric acid salt (PyBOP (R)), and, where necessary, with an additive such as 1-hydroxybenzotriazole 1 hydrate (HOBt), and the reaction mixture may be stirred while heating to produce the compound 2-h of the present invention.

Step (2-4): The compound 2-k of the present invention may be produced by reacting the mixture of the compound 2-d and the compound of 2-j with sodium cyanoborohydride, or sodium triacetoxyborohydride in an ether solvent such as tetrahydrofuran or dioxane, a halogen solvent such as methylene chloride or chloroform, an alcohol solvent such as methanol or ethanol or acetonitrile, in the presence or absence of a carboxylic acid such as acetic acid or trifluoroacetic acid.

General Synthesis Method 3

[Formula 4]

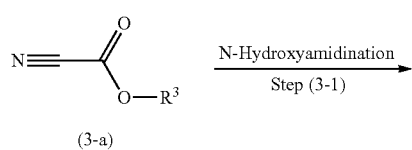

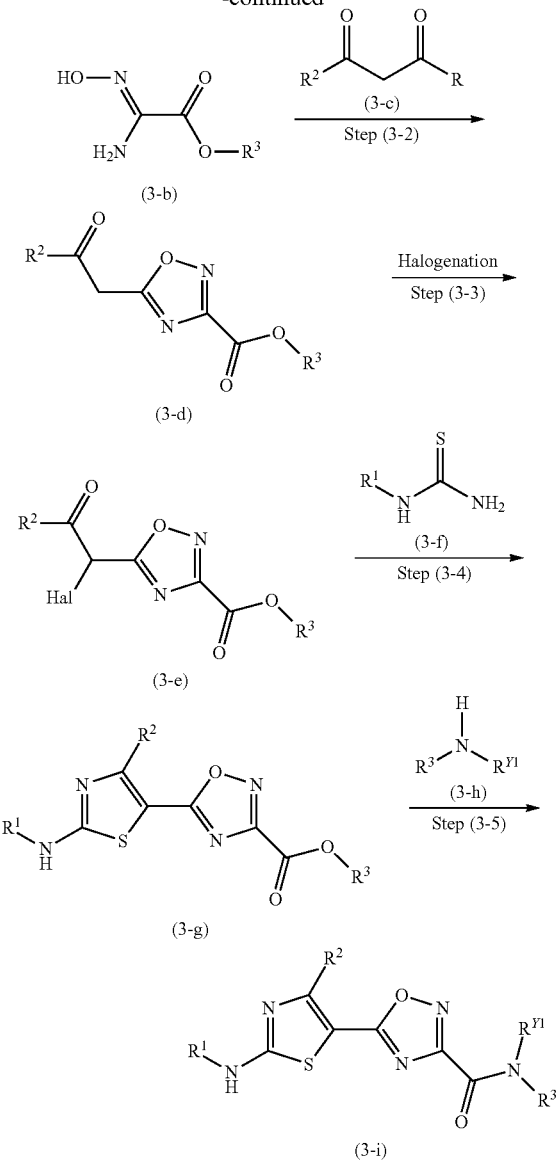

Step (3-1): The compound 3-a may be reacted with an aqueous solution of hydroxylamine or an aqueous solution of hydroxylamine obtained from hydroxyamine hydrochloride with an inorganic base such as sodium bicarbonate, potassium bicarbonate, sodium carbonate, potassium carbonate, sodium hydroxide, potassium hydroxide or lithium hydroxide, in water, an alcohol solvent such as methanol or ethanol or ether solvent such as tetrahydrofuran or dioxane, to produce the compound 3-b.

Step (3-2): According to the production method described in Tetrahedron Lett., 2007, 48, 2231, the compound 3-d may be produced by adding the compound 3-c to the compound 3-b and heated. The R in the compound 3-c is preferably a tert-butyl group.

Step (3-3): The compound 3-e may be produced by reacting the compound 3-d with a halogenation reagent such as tetra-n-butyl ammonium tribromide, N-chlorosuccinimide, N-bromosuccinimide, bromine or copper bromide (II) in an ether solvent such as tetrahydrofuran or dioxane, a halogen solvent such as methylene chloride, chloroform, carbon tetrachloride or a protic polar solvent such as water or acetic acid.

Step (3-4): The compound 3-g of the present invention may be produced by reacting the compound 3-e with the compound 3-f in an ether solvent such as tetrahydrofuran or dioxane, a halogen solvent such as methylene chloride or chloroform, an aromatic hydrocarbon solvent such as toluene or xylene, or an aprotic polar solvent such as N,N-dimethylformamide or N,N-dimethylacetamide, in the presence or absence of a base such as triethylamine or pyridine.

Step (3-5): The compound 3-i of the present invention may be produced by reacting the compound 3-g with the compound 3-h in water, an alcohol solvent such as methanol or ethanol, an ether solvent such as tetrahydrofuran or dioxane, or an aprotic polar solvent such as N,N-dimethylformamide or N,N-dimethylacetamide.

General Synthesis Method 4

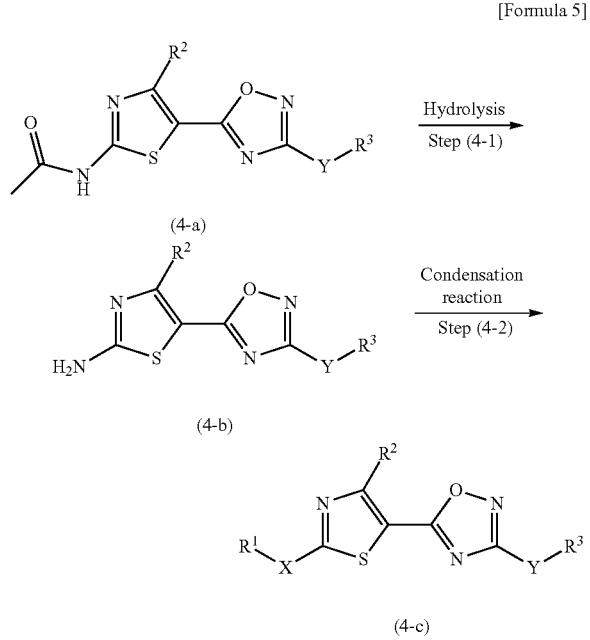

Step (4-1): The compound 4-b of the present invention may be produced by hydrolyzing the compound 4-a in water, an alcohol solvent such as methanol or ethanol, an ether solvent such as tetrahydrofuran or dioxane, using a mineral acid such as hydrochloric acid or an inorganic base such as sodium hydroxide or potassium hydroxide.

Step (4-2): The compound 4-c of the present invention may be produced by reacting the compound 4-b with various acyl chlorides, sulfonyl chlorides, chloroformates or isocyanates in an ether solvent such as tetrahydrofuran or dioxane, a halogen solvent such as methylene chloride or chloroform, an aromatic hydrocarbon solvent such as toluene or xylene, in the presence or absence of a base such as triethylamine or pyridine. The compound 4-c of the present invention may also be produced by reacting the compound 4-b with various carboxylic acids in the present or absence of a base such as triethylamine or pyridine, using a condensation agent such as DCC, EDC hydrochloride or PyBOP or an additive such as HOBt monohydrate. Alternatively, the compound 4-c of the present invention may be produced by reacting the compound 4-b of the present invention with N,N'-carbonyldiimidazole (CDI) and further reacting with various amines or alcohols.

The reaction may be carried out by selecting a suitable temperature ranging from −78° C. to the boiling point of the solvent used for the reaction and at normal temperature, under applied pressure, microwave irradiation, or the like.

In order to use the compound of the present invention as a pharmaceutical, the compound of the present invention may be made into tablets, granules, pills, capsules, powders, liquids, suspensions, injections, or the like by adding a diluent, a bulking agent, a pH-adjusting agent, a solubilizing agent, or the like typically used, by a routine pharmaceutical technology, which may be administered orally or as an injection or a liniment.

The compound of the present invention may be administered at one to several doses of 0.01 to 100 mg/kg a day per adult patient. The dosage is suitably variable according to the type of disease, patient's age, body weight, symptoms, etc.

Hereinafter, Examples and Test Examples are given to further describe the compound of the present invention in detail. In Examples, CDI means N,N'-carbonyldiimidazole, EDC means 1-(3-dimethylaminopropyl)-3-ethylcarbodiimide, HOBt means 1-hydroxybenzotriazole, Burgess reagent is (methoxycarbonylsulfamoyl)triethylammonium hydroxide inner salt, Dess-Martin reagent is 1,1,1-triacetoxy-1,1-dihydro-1,2-benziodoxol-3(1H)-one and TBAF means tetra-n-butyl ammonium fluoride.

The chemical shift shown in [ ] in the NMR data is derived from a minor ingredient of the E and Z isomers of the oxime structure, and the chemical shift shown in front of [ ] is derived from a major ingredient.

EXAMPLES

The compounds of Examples 1 to 54, 56 to 69, 71, 73 to 77, 79 to 89, 92 to 95 and 97 to 114 were synthesized by the same method as shown in General synthesis method 1. The compounds of Examples 55, 70, 72, 78, 90, 91 and 96 were synthesized by the same method as shown in General synthesis method 3. The compounds of Examples 115 to 176 were synthesized by the same method as the combined method of General synthesis methods 1 and 4. Hereinafter, the production methods are described in detail with reference to Example 1, Example 2, Example 3, Example 31, Example 84 and Example 87 as the synthesis examples which use the General synthesis method 1; Example 55 and Example 72 as the synthesis examples which use the General synthesis method 3; Example 115, Example 117 and Example 129 as the combined synthesis examples of the General synthesis methods 1 and 4.

Synthesis Example of General Synthesis Method 1

Example 1

N-{4-methyl-5-[3-(pyridin-3-yl)-1,2,4-oxadiazol-5-yl]-1,3-thiazol-2-yl}acetamide (1) An aqueous solution of 1M-sodium hydroxide (50 ml) was added to an ethanol solution (100 ml) of ethyl 2-amino-4-methylthiazole-5-carboxylate (3.0 g) and the mixture was stirred at room temperature for 26 hours. After distilling off the solvent, acetic acid was added thereto under ice cooling (pH=5). Water was added thereto, the resultant mixture was stirred, and the crystal was collected by filtration. The crystal was washed with water, thereby obtaining 2-amino-4-methyl-thiazole-5-carboxylic acid (2.5 g) as a colorless solid.

(2) Triethylamine (1.3 ml) and acetyl chloride (0.6 ml) were added to a tetrahydrofuran suspension (20 ml) of the compound obtained in Example 1-(1) (500 mg) under ice cooling, and the mixture was stirred at room temperature for 1 hour. Tetrahydrofuran (20 ml) was added to the reaction mixture and stirred at room temperature for 21 hours. The solvent was distilled off under reduced pressure, and water was added to the residue and stirred at room temperature for 1 hour. The obtained crystal was collected by filtration, washed with water, thereby obtaining 2-acetamido-4-methylthiazole-5-carboxylic acid (585 mg) as a colorless solid.

(3) Hydroxylamine hydrochloride (1.3 g) and sodium carbonate (2.0 g) were added to a mixed solution of 3-cyanopyridine in methanol (10 ml)/water (10 ml) and the mixture was stirred at 100° C. for 2.5 hours. After distilling off the solvent under reduced pressure, water was added to the residue and extracted with tetrahydrofuran, and the organic layer was washed with saturated brine. The organic layer was dried over magnesium sulfate and the solvent was distilled off under reduced pressure to obtain N'-hydroxypyridine-3-carboximidamide (1.3 g) as a colorless oily substance.

(4) Triethylamine (0.1 ml) was added to an N,N-dimethylformamide solution (3 ml) of the compound obtained in Example 1-(2) (72 mg), the compound obtained in Example 1-(3) (45 mg), EDC hydrochloride (76 mg) and HOBt monohydrate (54 mg), and the mixture was stirred at room temperature for 25 hours. Water was added to the reaction mixture, followed by extraction with ethyl acetate and the organic layer was washed with saturated brine. The organic layer was dried over magnesium sulfate and the solvent was distilled off under reduced pressure. Toluene (5 ml) was added to the residue and stirred at 130° C. for 7 hours. N,N-dimethylformamide (2 ml) was added to the reaction mixture and stirred at 130° C. for 18 hours.

After distilling off the solvent under reduced pressure, the residue was washed with chloroform/methanol, thereby obtaining the title compound (22 mg) as a colorless solid.

Example 2

N-[5-(3-tert-butyl-1,2,4-oxadiazol-5-yl)-4-methyl-1,3-thiazol-2-yl]acetamide (1) Using trimethyl acetonitrile (2.5 g), the same procedure as in Example 1-(3) was carried out, thereby obtaining N'-hydroxy-2,2-dimethylpropanimidamide (1.9 g) as a colorless solid.

(2) Using the compound obtained in Example 2-(1) (242 mg), the same procedure as in Example 1-(4) was carried out, thereby obtaining the title compound (16 mg) as a colorless solid.

Example 3

N-{4-methyl-5-[3-(pyrimidin-5-yl)-1,2,4-oxadiazol-5-yl]-1,3-thiazol-2-yl}acetamide (1) Using 5-cyanopyrimidine (1.0 g), the same procedure as in Example 1-(3) was carried out, thereby obtaining N'-hydroxypyrimidine-5-carboximidamide (1.3 g) as a light yellow solid.

(2) An N,N-dimethylformamide solution (15 ml) of the compound obtained in Example 3-(1) (200 mg), the compound obtained in Example 1-(2) (319 mg), EDC hydrochloride (334 mg) and HOBt monohydrate (235 mg) was stirred at room temperature for 15 hours. Water was added to the reaction mixture, followed by extraction with chloroform/methanol and the organic layer was washed with saturated brine. The organic layer was dried over magnesium sulfate and the solvent was distilled off under reduced pressure. Toluene (20 ml) and N,N-dimethylformamide (5 ml) were added to the residue and stirred at 130° C. for 16 hours. The solvent was distilled off under reduced pressure and the residue was washed with chloroform. The crude product was purified by column chromatography (silica gel 60 (acidic OH Type, KANTO CHEMICAL CO., INC.) and methanol/chloroform=0 to 5%) and the obtained solid was washed with chloroform, thereby obtaining the title compound (83 mg) as a colorless solid.

Example 31

N-{5-[3-(3-hydroxy-2,2-dimethylpropyl)-1,2,4-oxadiazol-5-yl]-4-methyl-1,3-thiazol-2-yl}acetamide (1) Sodium cyanide (902 mg) was added to a solution of 3-bromo-2,2-dimethylpropan-1-ol (2.1 g) in dimethyl sulfoxide (20 ml) and stirred at 100° C. for 10 hours in nitrogen atmosphere. Water was added to the reaction mixture, followed by extraction with tetrahydrofuran and the organic layer was washed with saturated brine. The organic layer was dried over sodium sulfate and the solvent was distilled off under reduced pressure, thereby obtaining 4-hydroxy-3,3-dimethylbutanenitrile (1.5 g) as a light yellow oily substance.

(2) Tert-butyldimethylchlorosilane (1.5 g) and imidazole (1.5 g) were added to a tetrahydrofuran solution (50 ml) of the compound obtained in Example 31-(1) (1.5 g), and stirred at room temperature for 30 minutes under nitrogen atmosphere. Water was added to the reaction mixture, followed by extraction with ethyl acetate and the organic layer was washed with saturated brine. The organic layer was dried over magnesium sulfate and the solvent was distilled off under reduced pressure. The residue was purified by column chromatography (silica gel 60 (acidic OH Type, KANTO CHEMICAL CO., INC.), ethyl acetate/n-hexane=5%), thereby obtaining 4-{[tert-butyl(dimethyl)silyl]oxy}-3,3-dimethylbutanenitrile (1.9 g) as a colorless oily substance.

(3) Using the compound obtained in Example 31-(2) (1.9 g), the same procedure as in Example 1-(3) was carried out, thereby obtaining 4-{[tert-butyl(dimethyl)silyl]oxy}-N'-hydroxy-3,3-dimethylbutanimidamide (158 mg) as a colorless oily substance.

(4) The compound obtained in Example 1-(2) (143 mg) and EDC hydrochloride (137 mg) were added to an N,N-dimethylacetamide solution (3 ml) of the compound obtained in Example 31-(3) (155 mg) and stirred at room temperature for 10 hours under nitrogen atmosphere. Molecular sieves (4A, 131 mg) was added to the reaction mixture and stirred at 120° C. for 4 hours under nitrogen atmosphere. TBAF (a 1M-tetrahydrofuran solution, 933 mg) was added to the reaction mixture and stirred at 80° C. for 6 hours under nitrogen atmosphere. Water was added to the reaction mixture, followed by extraction with tetrahydrofuran and the organic layer was washed with saturated brine. The organic layer was dried over magnesium sulfate and the solvent was distilled off under reduced pressure. The residue was purified by column chromatography (acidic OH Type silica gel (KANTO CHEMICAL Co., INC., silica gel 60N), methanol/chloroform=10%). The obtained solid was purified by column chromatography (NH Type silica gel (NH-DM1020, Fuji Silysia Chemical Ltd., methanol/chloroform=0 to 5%), thereby obtaining the title compound (23 mg) as a colorless solid.

Example 84

N-{5-[3-(2-methoxy-2-methylpropyl)-1,2,4-oxadiazol-5-yl]-4-methyl-1,3-thiazol-2-yl}acetamide (1) Dess-Martin reagent (15.0 g) was added to a chloroform solution (35 ml) of 3-methoxy-3-methyl-1-butanol (3.3 g) under ice cooling and stirred at room temperature for 5 hours. Chloroform was added to the reaction mixture and the organic layer was washed with an aqueous solution of 20 wt. % sodium thiosulfate, a saturated aqueous solution of sodium hydrogencarbonate and saturated brine. The organic layer was dried over magnesium sulfate and the solvent was distilled off under reduced pressure, thereby obtaining a crude product containing 3-methoxy-3-methylbutanal. Hydroxyamine hydrochloride (3.5 g) was added to a pyridine solution of the obtained crude product (30 ml) under ice cooling and stirred at room temperature overnight under nitrogen atmosphere. Ethyl acetate was added to the reaction mixture and the organic layer was washed with water, 1M-hydrochloric acid aqueous solution and saturated brine. The organic layer was dried over magnesium sulfate and the solvent was distilled off under reduced pressure. The residue was purified by column chromatography (KP-Sil, Biotage, ethyl acetate/n-hexane=10 to 50%), thereby obtaining (N-hydroxy-3-methoxy-3-methylbutan-1-imine (1.4 g) as a colorless oily substance.

(2) A Burgess reagent (3.8 g) was added to a solution of the compound obtained in Example 84-(1) (1.4 g) in tetrahydrofuran (25 ml) and stirred at room temperature for 1 hour under nitrogen atmosphere. The reaction mixture was concentrated under reduced pressure, ethanol (20 ml) and a 50% hydroxylamine aqueous solution (1.3 g) were added to the residue and stirred at 70° C. for 2.5 hours. A 50% hydroxylamine aqueous solution (1.3 g) was added to the reaction mixture and stirred at 70° C. for 1.5 hours. The reaction mixture was concentrated under reduced pressure and the residue was purified by column chromatography (SNAP KP-NH, Biotage, methanol/chloroform=0 to 10%), thereby obtaining N'-hydroxy-3-methoxy-3-methylbutanimidamide (0.93 g) as a green oily substance.

(3) Using the compound obtained in Example 84-(2) (0.93 g) and the compound obtained in Example 1-(2) (1.3 g), the same procedure as in Example 31-(4) was carried out, thereby obtaining the title compound (42 mg) as a colorless solid.

Example 87

N-{4-methyl-5-[3-(morpholin-4-yl)-1,2,4-oxadiazol-5-yl]-1,3-thiazol-2-yl}acetamide Triethylamine (3.2 ml) and cyanogen bromide (1.6 g) were added to a chloroform solution (20 ml) of morpholine (1.0 g) under ice cooling and stirred at room temperature overnight. Water was added to the reaction mixture, followed by extraction with chloroform and the organic layer was washed with saturated brine. The organic layer was dried over magnesium sulfate and the solvent was distilled off under reduced pressure, thereby obtaining a crude product containing morpholine-4-carbonitrile. Triethylamine (4.8 ml) and hydroxylamine hydrochloride (1.6 g) were added to a methanol solution (15 ml) of the obtained crude product and stirred at room temperature for 4 hours. The solvent was distilled off under reduced pressure and the residue was purified by column chromatography (KP-Sil, Biotage, methanol/chloroform=0 to 10%), thereby obtaining a crude product containing N'-hydroxymorpholine-4-carboximidamide. The compound obtained in Example 1-(2) (2.3 g) and EDC hydrochloride (2.7 g) were added to an N,N-dimethylformamide solution (20 ml) of the obtained crude product and stirred at room temperature for 2 hours under nitrogen atmosphere. The reaction mixture was stirred at 100° C. for 3 hours. The solvent was distilled off under reduced pressure and the residue was purified by column chromatography (KP-Sil, Biotage, methanol/chloroform=0 to 10%), (KP-NH, Biotage, methanol/chloroform=0 to 5%), thereby obtaining the title compound (247 mg) as a colorless solid.

Synthesis Example of General Synthesis Method 3

Example 55

Ethyl-5-[2-(acetylamino)-4-methyl-1,3-thiazol-5-yl]-1,2,4-oxadiazol-3-carboxylate (1) Using ethyl cyanoformate (5.0 g), the same procedure as in Example 1-(3) was carried out, thereby obtaining ethyl 2-amino(hydroxyimino)ethanoate (4.6 g) as a colorless solid.

(2) tert-Butyl acetoacetate (1.3 ml) was added to the compound obtained in Example 55-(1) (500 mg) and stirred at 120° C. for 6 hours. The reaction mixture was purified by column chromatography (KP-Sil, Biotage, ethyl acetate/n-hexane=20 to 70%), thereby obtaining ethyl 5-(2-oxopropyl)-1,2,4-oxadiazole-3-carboxylate (344 mg) as a yellow solid.

(3) Tetra-n-butyl ammonium tribromide (363 mg) was added to a tetrahydrofuran solution (5 ml) of the compound obtained in Example 55-(2) (142 mg), and the mixture was stirred at room temperature for 3 hours. Tetra-n-butyl ammonium tribromide (174 mg) was added to the reaction mixture and stirred at room temperature for 3 hours. N-acetyl thiourea (89 mg) was added to the residue and stirred at 70° C. for 16 hours. Water was added to the reaction mixture, followed by extraction with ethyl acetate and the organic layer was washed with saturated brine. The organic layer was dried over magnesium sulfate and the solvent was distilled off under reduced pressure. The residue was purified by column chromatography (KP-NH, Biotage, ethyl acetate/n-hexane=50 to 99%), thereby obtaining the title compound (27 mg) as a colorless solid.

Example 72

N-{4-methyl-5-[3-(morpholin-4-ylcarbonyl)-1,2,4-oxadiazol-5-yl]-1,3-thiazol-2-yl}acetamide Morpholine (0.6 ml) was added to an ethanol suspension of the compound (100 mg) obtained in Example 55-(3) and stirred at 80° C. for 17 hours. After distilling off the solvent under reduced pressure, the residue was purified by column chromatography (KP-Sil, Biotage, ethyl acetate/n-hexane=20 to 99%), thereby obtaining the title compound (71 mg) as a colorless solid.

Synthesis Example of Combined General Synthesis Methods 1 and 4

Example 115

2-Methyl-N-{4-methyl-5-[3-(pyridin-3-yl)-1,2,4-oxadiazol-5-yl]-1,3-thiazol-2-yl}propanamide (1) Using the compound (6.3 g) obtained in Example 1-(1) and the compound (5.0 g) obtained in Example 1-(3), the same procedure as in Example 3-(2) was carried out, thereby obtaining 4-methyl-5-[3-(pyridin-3-yl)-1,2,4-oxadiazol-5-yl]-1,3-thiazol-2-amine (3.5 g) as a yellow solid.

(2) Isobutyryl chloride (0.03 ml) and pyridine (1 ml) were added to a chloroform suspension (3 ml) of the compound (50 mg) obtained in Example 115-(1) and stirred at 65° C. for 7 hours. Water was added to the reaction mixture, followed by extraction with chloroform-methanol and the organic layer was washed with saturated brine. The organic layer was dried over magnesium sulfate and the solvent was distilled off under reduced pressure. The residue was purified by column chromatography (silica gel 60 (acidic OH Type, KANTO CHEMICAL CO., INC.,), methanol/chloroform=0 to 5%). The obtained solid was washed with chloroform, thereby obtaining the title compound (22 mg) as a light brown solid.

Example 117

Tert-butyl N-({4-methyl-5-[3-(pyridin-3-yl)-1,2,4-oxadiazol-5-yl]-1,3-thiazol-2-yl}carbamoyl)-β-alaninate CDI (469 mg) and pyridine (0.31 ml) were added to a chloroform suspension (20 ml) of the compound (500 mg) obtained in Example 115-(1) and stirred at 80° C. for 16 hours. β-Alanine-tert-butyl ester hydrochloride (877 mg), pyridine (0.47 ml) and N,N-dimethylformamide (5 ml) were added to the reaction mixture and stirred at 80° C. for 3 hours. After distilling off the solvent under reduced pressure, the residue was purified by column chromatography (NH Type silica gel (NH-DM1020, Fuji Silysia Chemical Ltd., ethyl acetate/n-hexane=50 to 99%, methanol/chloroform=0 to 5%), thereby obtaining the title compound (1.2 g) as a light yellow solid.

Example 129

Tert-butyl-3-[({4-methyl-5-[3-(pyridin-3-yl)-1,2,4-oxadiazol-5-yl]-1,3-thiazol-2-yl}carbamoyl)oxy] propanoate Using the compound (100 mg) obtained in Example 115-(1) and tert-butyl 3-hydroxypropionate (1.5 ml), the same procedure as in Example 117 was carried out, thereby obtaining the title compound (101 mg) as a colorless solid.

Tables 1 to 11 below show the structural formulae and NMR values of Examples 1 to 113. In the tables, the compound with a "—" shown in the Y column means that Y is a single bond.

[Formula 6]

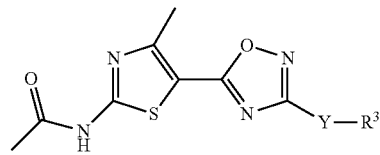

(2)

TABLE 1

| Example | Y | R3 | $^1$H NMR (δ ppm) |
|---|---|---|---|
| 1 | — | 3-pyridyl | (600 MHz, DMSO-d$_6$) 2.22 (s, 3 H) 2.74 (s, 3 H) 7.40-7.79 (m, 1 H) 8.24-8.52 (m, 1 H) 8.66-8.89 (m, 1 H) 9.07-9.31 (m, 1 H) 12.75 (brs, 1 H) |
| 2 | — | tert-butyl | (200 MHz, CHLOROFORM-d$_6$) 1.41 (s, 9 H) 2.30 (s, 3 H) 2.72 (s, 3 H) 9.11 (brs, 1 H) |
| 3 | — | 5-pyrimidinyl | (200 MHz, DMSO-d$_6$) 2.22 (s, 3 H) 2.74 (s, 3 H) 9.40 (s, 2 H) 9.42 (s, 1 H) 12.72 (brs, 1 H) |
| 4 | — | 6-methoxy-3-pyridyl | (200 MHz, DMSO-d$_6$) 2.21 (s, 3 H) 2.71 (s, 3 H) 3.95 (s, 3 H) 7.01 (dd, J = 8.4, 0.8 Hz, 1 H) 8.26 (dd, J = 8.4, 2.2 Hz, 1 H) 8.82 (d, J = 2.2 Hz, 1 H) 12.49-12.87 (brs, 1 H) |
| 5 | — | 6-(pyridin-3-ylmethoxy)-3-pyridyl | (200 MHz, DMSO-d$_6$) 2.21 (s, 3 H) 2.71 (s, 3 H) 5.25 (s, 2 H) 7.25 (d, J = 8.8 Hz, 2 H) 7.40-7.50 (m, 1 H) 7.86-8.05 (m, 3 H) 8.56 (brs, 1 H) 8.72 (brs, 1 H) 12.69 (brs, 1 H) |

TABLE 1-continued

| Example | Y | R3 | ¹H NMR (d ppm) |
|---|---|---|---|
| 6 | — | 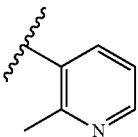 [SMILES: *c1cccnc1C] | (600 MHz, DMSO-d₆) 2.22 (s, 3 H) 2.71 (s, 3 H) 2.80 (s, 3 H) 7.45 (dd, J = 7.8, 4.6 Hz, 1 H) 8.30-8.34 (m, 1 H) 8.64 (dd, J = 4.6, 1.8 Hz, 1 H) 12.74 (brs, 1 H) |
| 7 | — | 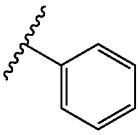 [SMILES: *c1ccccc1] | (200 MHz, DMSO-d₆) 2.22 (s, 3 H) 2.72 (s, 3 H) 7.52-7.64 (m, 3 H) 8.00-8.10 (m, 2 H) 12.72 (brs, 1 H) |
| 8 | — | 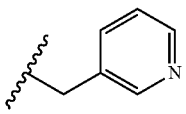 | (200 MHz, DMSO-d₆) 2.17 (s, 3 H) 2.62 (s, 3 H) 4.18 (s, 2 H) 7.38 (ddd, J = 7.9, 4.8, 0.9 Hz, 1 H) 7.77 (m, J = 7.9 Hz, 1 H) 8.48 (dd, J = 4.8, 1.7 Hz, 1 H) 8.59 (d, J = 1.7 Hz, 1H) |
| 9 | — | 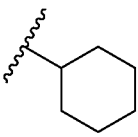 [SMILES: *C1CCCCC1] | (200 MHz, CHLOROFORM-d) 1.19-2.14 (m, 10 H) 2.30 (s, 3 H) 2.72 (s, 3 H) 2.84 (tt, J = 11.2, 3.6 Hz, 1 H) 9.83 (brs, 1 H) |
| 10 | — | 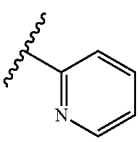 [SMILES: *c1ccccn1] | (200 MHz, DMSO-d₆) 2.22 (s, 3 H) 2.73 (s, 3 H) 7.57-7.69 (m, 1 H) 7.96-8.19 (m, 2 H) 8.75-8.83 (m, 1 H) 12.73 (brs, 2 H) |
| 11 | — | 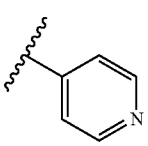 [SMILES: *c1ccncc1] | (200 MHz, DMSO-d₆) 2.22 (s, 3 H) 2.73 (s, 3 H) 7.94-8.01 (m, 2 H) 8.82 (d, J = 5.7 Hz, 2 H) 12.74 (brs, 1 H) |

TABLE 2

| Example | Y | R3 | ¹H NMR (d ppm) |
|---|---|---|---|
| 12 | — | 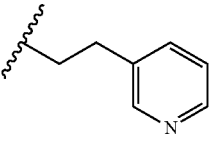 [SMILES: *CCc1cccnc1] | (200 MHz, DMSO-d₆) 2.20 (s, 3 H) 2.64 (s, 3 H) 3.03-3.12 (m, 4 H) 7.25-7.37 (m, 1 H) 7.68-7.73 (m, 1 H) 8.32-8.58 (m, 2 H) 12.67 (brs, 1 H) |
| 13 | — | 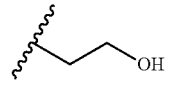 | (200 MHz, DMSO-d₆) 2.20 (s, 3 H) 2.65 (s, 3 H) 2.86 (t, J = 6.2 Hz, 2 H) 3.79 (brt, J = 6.2 Hz, 2 H) 4.82 (brs, 1 H) 12.70 (brs, 1 H) |
| 14 | — | 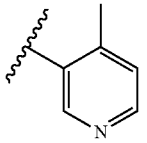 [SMILES: *c1cnccc1C] | (200 MHz, DMSO-d₆) 2.22 (s, 3 H) 2.62 (s, 3 H) 2.73 (s, 3 H) 7.48 (d, J = 4.8 Hz, 1 H) 8.62 (d, J = 4.8 Hz, 1 H) 9.06 (s, 1 H) |
| 15 | — | 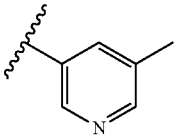 [SMILES: *c1cncc(C)c1] | (200 MHz, DMSO-d₆) 2.21 (s, 3 H) 2.41 (s, 3 H) 2.71 (s, 3 H) 8.12-8.23 (m, 1 H) 8.58-8.67 (m, 1 H) 8.99 (m, 1 H) 12.71 (brs, 1H) |

TABLE 2-continued

| Example | Y | R3 | ¹H NMR (d ppm) |
|---|---|---|---|
| 16 | — | 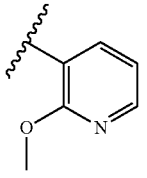 [SMILES: *c1cccnc1OC] | (200 MHz, DMSO-d₆) 2.21 (s, 3 H) 2.71 (s, 3 H) 4.00 (s, 3 H) 7.22 (dd, J = 7.5, 4.8 Hz, 1 H) 8.33-8.42 (m, 2 H) 12.72 (brs, 1 H) |
| 17 | — | 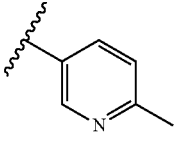 [SMILES: *c1ccc(C)nc1] | (200 MHz, DMSO-d₆) 2.21 (s, 3 H) 2.57 (s, 3 H) 2.71 (s, 3 H) 7.47 (d, J = 8.0 Hz, 1 H) 8.26 (dd, J = 8.0, 2.2 Hz, 1 H) 9.05 (d, J = 2.2 Hz, 1 H) 12.73 (brs, 1 H) |
| 18 | — | 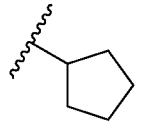 [SMILES: *C1CCCC1] | (200 MHz, CHLOROFORM-d) 1.65-2.19 (m, 8 H) 2.30 (s, 3 H) 2.73 (s, 3 H) 3.15-3.36 (m, 1 H) 10.05 (brs, 1 H) |
| 19 | — | 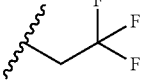 | (600 MHz, DMSO-d₆) 2.21 (s, 3 H) 2.66 (s, 3 H) 4.11 (q, J = 10.9 Hz, 2 H) 12.73 (brs, 1 H) |
| 20 | — | 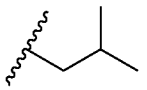 [SMILES: *CC(C)C] | (200 MHz, CHLOROFORM-d) 1.03 (d, J = 7.0 Hz, 6 H) 2.19 (m, 1H) 2.27 (s, 3 H) 2.64 (d, J = 7.0 Hz, 2 H) 2.73 (s, 3 H) 9.61 (brs, 1 H) |
| 21 | — | 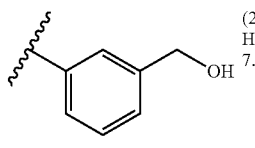 | (200 MHz, DMSO-d₆) 2.22 (s, 3 H) 2.72 (s, 3 H) 4.61 (d, J = 5.7 Hz, 2 H) 5.39 (t, J = 5.1 Hz, 1 H) 7.47-7.58 (m, 2 H) 7.86-7.97 (m, 1 H) 8.00-8.06 (m, 1 H) 12.71 (brs, 1 H) |
| 22 | — | 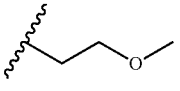 [SMILES: *CCOC] | (200 MHz, CHLOROFORM-d) 2.30 (s, 3 H) 2.72 (s, 3 H) 3.06 (t, J = 6.6 Hz, 2 H) 3.40 (s, 3 H) 3.83 (t, J = 6.6 Hz, 2 H) 9.56 (brs, 1 H) |

TABLE 3

| Example | Y | R3 | ¹H NMR (d ppm) |
|---|---|---|---|
| 23 | — | 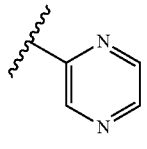 [SMILES: *c1cnccn1] | (200 MHz, DMSO-d₆) 2.22 (s, 3 H) 2.73 (s, 3 H) 8.84-8.91 (m, 2 H) 9.27-9.31 (m, 1 H) 12.74 (brs, 1 H) |
| 24 | — | 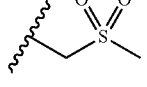 | (200 MHz, DMSO-d₆) 2.21 (s, 3 H) 2.67 (s, 3 H) 3.22 (s, 3H) 4.89 (s, 2 H) 12.73 (brs, 1 H) |
| 25 | — | 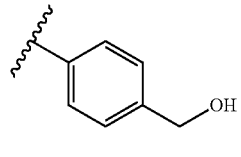 [SMILES: *c1ccc(CO)cc1] | (600 MHz, DMSO-d₆) 2.22 (s, 3 H) 2.73 (s, 3 H) 4.59 (s, 2 H) 5.36 (t, J = 5.7 Hz, 1 H) 7.53 (d, J = 8.3 Hz, 2 H) 7.98-8.05 (m, 2 H) 12.71 (brs, 1 H) |
| 26 | — | 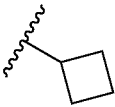 [SMILES: *C1CCC1] | (200 MHz, CHLOROFORM-d) 1.95-2.55 (s, 6 H) 2.31 (s, 3H) 2.75 (s, 3 H) 3.70 (quin, J = 8.5 Hz, 1 H) 10.05 (brs, 1 H) |

TABLE 3-continued

| Example | Y | R3 | ¹H NMR (d ppm) |
|---|---|---|---|
| 27 | — | 3-hydroxyphenyl | (600 MHz, DMSO-d₆) 2.21 (s, 3 H) 2.72 (s, 3 H) 6.91-7.04 (m, 1 H) 7.30-7.54 (m, 3 H) 9.85 (s, 1 H) 12.71 (brs, 1 H) |
| 28 | — | 3-(2-hydroxyethyl)phenyl | (600 MHz, DMSO-d₆) 2.22 (s, 3 H) 2.73 (s, 3 H) 2.83 (t, J = 6.7 Hz, 2 H) 3.63-3.70 (m, 2 H) 4.68 (t, J = 5.3 Hz, 1 H) 7.43-7.53 (m, 2 H) 7.86-7.93 (m, 2 H) 12.71 (brs, 1 H) |
| 29 | — | 2-(hydroxymethyl)phenyl | (600 MHz, DMSO-d₆) 2.22 (s, 3 H) 2.72 (s, 3 H) 4.87 (s, 2 H) 5.31 (t, J = 5.3 Hz, 1 H) 7.42-7.49 (m, 1 H) 7.58-7.65 (m, 1 H) 7.71-7.85 (m, 1 H) 7.93-8.05 (m, 1 H) 12.71 (brs, 1 H) |
| 30 | — | 4-acetoxybutyl | (200 MHz, CHLOROFORM-d) 2.02-2.10 (m, 3 H) 2.07-2.22 (m, 2 H) 2.29 (s, 3 H) 2.73 (s, 3 H) 2.88 (t, J = 7.0 Hz, 2 H) 4.19 (t, J = 7.0 Hz, 2 H) 9.83 (brs, 1 H) |
| 31 | — | 3-hydroxy-2,2-dimethylpropyl | (200 MHz, CHLOROFORM-d) 1.03 (s, 6 H) 2.32 (s, 3 H) 2.71 (s, 3 H) 2.77 (s, 2 H) 2.90 (t, J = 6.8 Hz, 1 H) 3.40 (d, J = 6.8 Hz, 2 H) |
| 32 | — | 5-hydroxypyridin-3-yl | (600 MHz, DMSO-d₆) 2.21 (s, 3 H) 2.72 (s, 3 H) 7.71-7.78 (m, 1 H) 8.34 (d, J = 2.8 Hz, 1 H) 8.68 (d, J = 1.4 Hz, 1H) |
| 33 | — | 4-hydroxybutyl | (200 MHz, DMSO-d₆) 1.85 (m, 2 H) 2.19 (s, 3 H) 2.64 (s, 3 H) 2.78 (t, J = 6.6 Hz, 2 H) 3.47 (m, 2 H) 4.59 (brs, 1 H) 12.58 (brs, 1 H) |

TABLE 4

| Example | Y | R3 | ¹H NMR (d ppm) |
|---|---|---|---|
| 34 | — | 3-hydroxy-2,2-dimethylpropyl (variant) | (200 MHz, CHLOROFORM-d) 1.35 (s, 6 H) 2.32 (s, 3 H) 2.72 (s, 3 H) 2.99 (s, 2 H) 3.42 (brs, 1 H) 9.68 (brs, 1 H) |
| 35 | — | vinyl | (200 MHz, DMSO-d₆) 2.21 (s, 3 H) 2.67 (s, 3 H) 5.90 (dd, J = 10.6, 1.3 Hz, 7 H) 6.38 (dd, J = 17.1, 1.3 Hz, 7 H) 6.83 (dd, J = 17.1, 10.6 Hz, 7 H) 12.71 (brs, 1 H) |
| 36 | — | 3-(hydroxymethyl)benzyl | (200 MHz, DMSO-d₆) 2.17 (s, 3 H) 2.62 (s, 3 H) 4.10 (s, 2 H) 4.47 (s, 2 H) 7.08-7.39 (m, 4 H) |
| 37 | — | 5-(methoxycarbonyl)pyridin-3-yl | (600 MHz, DMSO-d₆) 2.22 (s, 3 H) 2.73 (s, 3 H) 3.96 (s, 3 H) 8.74 (t, J = 2.1 Hz, 1 H) 9.26 (d, J = 2.3 Hz, 1 H) 9.41 (s, 1 H) 12.74 (brs, 1 H) |

TABLE 4-continued

| Example | Y | R3 | ¹H NMR (d ppm) |
|---|---|---|---|
| 38 | — | (2-hydroxybutyl, methyl-substituted) | (200 MHz, CHLOROFORM-d) 1.38 (d, J = 6.2 Hz, 3 H) 2.32 (s, 3 H) 2.70 (s, 3 H) 2.78-3.07 (m, 2 H) 3.20 (brs, 1 H) 4.23-4.41 (m, 1 H) 9.78 (brs, 1 H) |
| 39 | — | (1-methyl-2-oxo-1,2-dihydropyridin-5-yl) | (600 MHz, DMSO-d₆) 2.21 (s, 3 H) 2.71 (s, 3 H) 3.57 (s, 3 H) 6.56 (d, J = 9.6 Hz, 1 H) 7.93 (dd, J = 9.4, 2.5 Hz, 1 H) 8.53 (d, J = 2.8 Hz, 1H) 12.70 (brs, 1 H) |
| 40 | — | (2-oxo-1,2-dihydropyridin-5-yl) | (600 MHz, DMSO-d₆) 2.21 (s, 3 H) 2.69 (s, 3 H) 6.51 (d, J = 9.6 Hz, 1 H) 7.93 (dd, J = 9.6, 2.8 Hz, 1 H) 8.06 (d, J = 2.3 Hz, 1 H) 12.13 (brs, 1 H) 12.67 (brs, 1 H) |
| 41 | — | (3-methyloxetan-3-yl)methyl | (200 MHz, CHLOROFORM-d) 1.40 (s, 3 H) 2.31 (s, 3 H) 2.71 (s, 3 H) 3.11 (s, 2 H) 4.46 (d, J = 6.2 Hz, 2 H) 4.75 (d, J = 6.2 Hz, 2 H) 8.95 (brs, 1 H) |
| 42 | — | 2,2-bis(hydroxymethyl) | (600 MHz, DMSO-d₆) 0.80 (s, 3 H) 2.20 (s, 3 H) 2.65 (s, 3 H) 2.67 (s, 2 H) 3.26-3.37 (m, 4 H) 4.49 (t, J = 5.3 Hz, 2 H) 12.64 (brs, 1 H) |
| 43 | — | 3-amino-2,2-dimethylpropyl | (600 MHz, DMSO-d₆) 0.90 (s, 6 H) 2.18 (s, 3 H) 2.43 (s, 2 H) 2.62-2.65 (m, 5 H) |
| 44 | — | 2,2-dimethyl-3-(methylsulfonylamino)propyl | (200 MHz, CHLOROFORM-d) 1.08 (s, 6 H) 2.32 (s, 3 H) 2.71 (s, 3 H) 2.73 (s, 2 H) 2.96-3.02 (m, 5 H) 5.23 (t, J = 7.0 Hz, 1 H) 9.01 (brs, 1 H) |

TABLE 5

| Example | Y | R3 | ¹H NMR (d ppm) |
|---|---|---|---|
| 45 | — | (tetrahydro-2H-pyran-4-yl)methyl | (200 MHz, CHLOROFORM-d) 1.66 (m, 4 H) 1.98-2.22 (m, 1 H) 2.31 (s, 3 H) 2.70-2.74 (m, 5 H) 3.41 (m, 2 H) 3.92-4.03 (m, 2 H) 9.55 (brs, 1 H) |
| 46 | — | 2-ethyl-2-(hydroxymethyl)butyl | (600 MHz, CHLOROFORM-d) 0.84-0.94 (m, 6 H) 1.26-1.44 (m, 4 H) 2.31 (s, 3 H) 2.70 (s, 3 H) 2.75 (s, 2 H) 2.96 (brs, 1 H) 3.41 (brs, 2 H) 8.98 (brs, 1 H) |
| 47 | — | 3-hydroxy-3-methylbutyl | (200 MHz, DMSO-d₆) 1.15 (s, 6 H) 1.77 (m, 2 H) 2.20 (s, 3 H) 2.64 (s, 3 H) 2.77 (m, 2 H) 4.37 (s, 1 H) 12.66 (brs, 1 H) |
| 48 | — | (1-(hydroxymethyl)cyclopropyl)methyl | (200 MHz, CHLOROFORM-d) 0.61 (m, 4 H) 2.31 (s, 3 H) 2.71 (s, 3 H) 2.90 (s, 2 H) 3.57 (s, 2 H) 3.64 (s, 1 H) |

TABLE 5-continued

| Example | Y | R3 | $^1$H NMR (d ppm) |
|---|---|---|---|
| 49 | — | 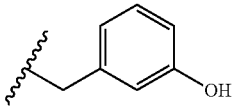 [SMILES: *Cc1cccc(O)c1] | (600 MHz, DMSO-d$_6$) 2.19 (s, 3 H) 2.63 (s, 3 H) 4.01 (s, 2 H) 6.62-6.67 (m, 1 H) 6.71-6.77 (m, 2 H) 7.08-7.14 (m, 1 H) 9.39 (s, 1 H) 12.65 (brs, 1 H) |
| 50 | — | 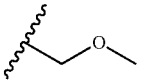 [SMILES: *COC] | (200 MHz, CHLOROFORM-d) 2.31 (s, 3 H) 2.75 (s, 3 H) 3.52 (s, 3 H) 4.62 (s, 2 H) 9.71 (brs, 1 H) |
| 51 | — |  | (600 MHz, CHLOROFORM-d) 1.02 (s, 6 H) 2.30 (s, 3 H) 2.72 (s, 3 H) 2.76 (s, 2 H) 3.19 (s, 2 H) 3.38 (s, 3 H) 8.96 (brs, 1 H) |
| 52 | — | 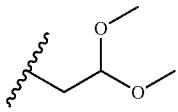 [SMILES: *CC(OC)OC] | (600 MHz, CHLOROFORM-d) 2.30 (s, 3 H) 2.72 (s, 3 H) 3.11 (d, J = 6.0 Hz, 2 H) 3.40 (s, 6 H) 4.96 (t, J = 6.0 Hz, 1 H) 9.20 (brs, 1H) |
| 53 | — |  | (200 MHz, CHLOROFORM-d) 1.03 (d, J = 7.0 Hz, 3 H) 2.15-2.30 (m, 1 H) 2.30 (s, 3 H) 2.68-2.97 (m, 2 H) 2.72 (s, 3 H) 3.50-3.71 (m, 2 H) 9.17 (brs, 1 H) |
| 54 | — | 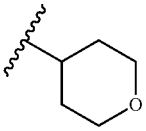 [SMILES: *C1CCOCC1] | (600 MHz, CHLOROFORM-d) 1.96-2.03 (m, 4 H) 2.31 (s, 3 H) 2.72 (s, 3 H) 3.06-3.12 (m, 1 H) 3.53-3.59 (m, 2 H) 4.03-4.09 (m, 2 H) 8.99 (brs, 1 H) |
| 55 |  | 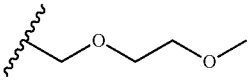 [SMILES: *COCCOC] | (600 MHz, CHLOROFORM-d) 1.46 (t, J = 7.1 Hz, 3 H) 2.32 (s, 3 H) 2.77 (s, 3 H) 4.53 (q, J = 7.3 Hz, 2 H) 8.98 (brs, 1 H) |

TABLE 6

| Example | Y | R3 | $^1$H NMR (d ppm) |
|---|---|---|---|
| 56 | — | 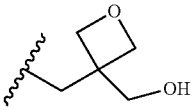 [SMILES: *CC1(CO)COC1] | (600 MHz, CHLOROFORM-d) 2.31 (s, 3 H) 2.72 (s, 3 H) 3.40 (s, 3 H) 3.61-3.63 (m, 2 H) 3.79-3.82 (m, 2 H) 4.74 (s, 2 H) |
| 57 | — | 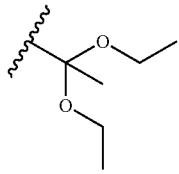 [SMILES: *C(C)(OCC)OCC] | (600 MHz, CHLOROFORM-d) 2.31 (s, 3 H) 2.32-2.35 (m, 1 H) 2.70 (s, 3 H) 3.26 (s, 2 H) 3.92 (d, J = 5.0 Hz, 2 H) 4.52 (d, J = 6.4 Hz, 2 H) 4.66 (d, J = 6.4 Hz, 2 H) 8.95 (brs, 1 H) |
| 58 | — | 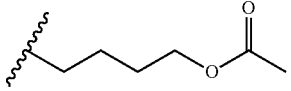 [SMILES: *CCCCOC(C)=O] | (200 MHz, CHLOROFORM-d) 1.28 (t, J = 7.0 Hz, 4 H) 1.78 (s, 3 H) 2.31 (s, 3 H) 2.74 (s, 3 H) 3.47-3.77 (m, 6 H) 10.11 (brs, 1 H) |
| 59 | — |  | (200 MHz, CHLOROFORM-d) 1.72-1.79 (m, 4 H) 2.06 (s, 3 H) 2.31 (s, 3 H) 2.73 (s, 3 H) 2.84 (t, J = 7.0 Hz, 2 H) 4.12 (t, J = 7.0 Hz, 2 H) 9.88 (brs, 1 H) |
| 60 |  |  | (200 MHz, DMSO-d$_6$) 2.21 (s, 3 H) 2.64 (s, 3 H) 2.68 (s, 3 H) 12.82 (brs, 1H) |

TABLE 6-continued

| Example | Y | R3 | ¹H NMR (d ppm) |
|---|---|---|---|
| 61 | — | 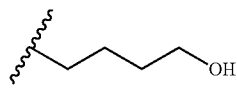 [SMILES: *CCCCO] | (200 MHz, DMSO-d$_6$) 2.20 (s, 3 H) 2.64 (s, 3 H) 2.73 (t, J = 7.5 Hz, 2 H) 3.43 (m, 2 H) 4.43 (brs, 1 H) 12.67 (brs, 1 H) |
| 62 | — | 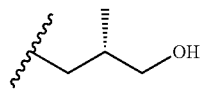 [SMILES: *C[C@H](C)CO] | (200 MHz, DMSO-d$_6$) 0.90 (d, J = 7.0 Hz, 3 H) 1.94-2.12 (m, 1 H) 2.20 (s, 3 H) 2.65 (s, 3 H) 2.86 (dd, J = 14.5, 5.3 Hz, 1 H) 4.64 (brs, 1 H) 12.67 (brs, 1 H) |
| 63 | — | 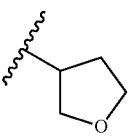 [SMILES: *C1CCOC1] | (600 MHz, CHLOROFORM-d) 2.31 (s, 3 H) 2.33-2.39 (m, 2 H) 2.72 (s, 3 H) 3.64 (dt, J = 14.7, 7.3 Hz, 1 H) 3.94-4.08 (m, 3 H) 4.16-4.21 (m, 1 H) 9.18 (brs, 1 H) |
| 64 | — | 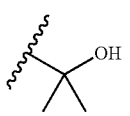 [SMILES: *C(C)(C)O] | (600 MHz, DMSO-d$_6$) 1.52 (s, 6 H) 2.20 (s, 3 H) 2.65 (s, 3 H) 5.59 (s, 1 H) 12.65 (brs, 1 H) |
| 65 | — | 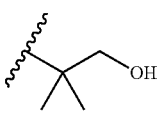 [SMILES: *C(C)(C)CO] | (600 MHz, DMSO-d$_6$) 1.28 (s, 6 H) 2.20 (s, 3 H) 2.64 (s, 3 H) 3.54 (d, J = 5.5 Hz, 2 H) 4.82 (t, J = 5.5 Hz, 1 H) 12.63 (brs, 1 H) |
| 66 | — | 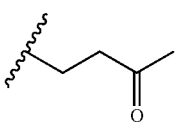 [SMILES: *CCC(C)=O] | (200 MHz, CHLOROFORM-d) 2.24 (s, 3 H) 2.31 (s, 3 H) 2.71 (s, 3 H) 2.93-3.11 (m, 4 H) 9.59 (brs, 1 H) |

TABLE 7

| Example | Y | R3 | ¹H NMR (d ppm) |
|---|---|---|---|
| 67 | — | 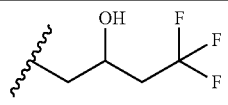 | (600 MHz, DMSO-d$_6$) 2.20 (s, 3 H) 2.42-2.63 (m, 2 H) 2.65 (s, 3 H) 2.83-2.97 (m, 2 H) 4.27 (brs, 1 H) 5.32 (d, J = 6.4 Hz, 1 H) 12.66 (brs, 1 H) |
| 68 | — | 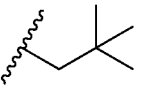 | (200 MHz, CHLOROFORM-d) 1.06 (s, 9 H) 2.31 (s, 3 H) 2.68 (s, 2 H) 2.73 (s, 3 H) 9.57 (brs, 1 H) |
| 69 | — | 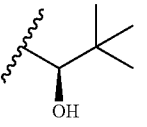 [SMILES: *[C@H](O)C(C)(C)C] | (200 MHz, CHLOROFORM-d) 1.05 (s, 9 H) 1.63 (s, 3 H) 2.32 (s, 3 H) 2.73 (s, 3 H) 2.82 (d, J = 8.1 Hz, 1 H) 4.56 (d, J = 8.1 Hz, 1 H) 9.47 (brs, 1 H) |
| 70 | 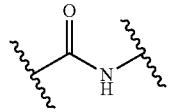 | H | (600 MHz, DMSO-d$_6$) 2.21 (s, 3 H) 2.68 (s, 3 H) 8.13 (s, 1 H) 8.32 (s, 1 H) 12.72 (brs, 1 H) |
| 71 | — | 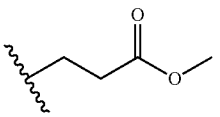 [SMILES: *CCC(=O)OC] | (600 MHz, CHLOROFORM-d) 2.31 (s, 3 H) 2.71 (s, 3 H) 2.85 (t, J = 7.3 Hz, 2 H) 3.12 (t, J = 7.3 Hz, 2 H) 3.73 (s, 3 H) 8.93 (brs, 1 H) |
| 72 | 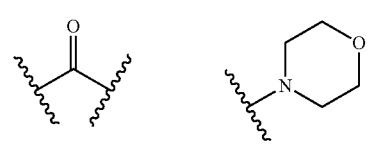 | 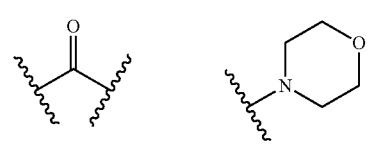 | (600 MHz, DMSO-d$_6$) 2.21 (s, 3 H) 2.67 (s, 3 H) 3.51-3.62 (m, 4 H) 3.68 (s, 4 H) 12.74 (brs, 1 H) |

TABLE 7-continued

| Example | Y | R3 | ¹H NMR (d ppm) |
|---|---|---|---|
| 73 | — | 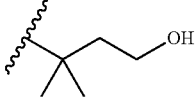 [SMILES: *C(C)(C)CCO] | (600 MHz, CHLOROFORM-d) 1.44 (s, 6 H) 2.03 (t, J = 6.7 Hz, 2 H) 2.30 (s, 3 H) 2.69 (s, 3 H) 3.75 (t, J = 6.7 Hz, 2 H) 9.20 (brs, 1 H) |
| 74 | — | 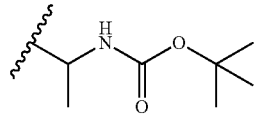 [SMILES: *C(C)NC(=O)OC(C)(C)C] | (600 MHz, CHLOROFORM-d) 1.47 (s, 9 H) 1.56 (d, J = 6.9 Hz, 3 H) 2.31 (s, 3 H) 2.69 (s, 3 H) 5.03-5.21 (m, 2 H) 9.43 (brs, 1 H) |
| 75 | — | 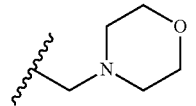 [SMILES: *CN1CCOCC1] | (600 MHz, CHLOROFORM-d) 2.31 (s, 3 H) 2.62-2.68 (m, 4 H) 2.72 (s, 3 H) 3.70-3.82 (m, 6 H) 9.18 (brs, 1 H) |
| 76 | — | 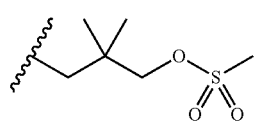 [SMILES: *CC(C)(C)COS(C)(=O)=O] | (200 MHz, CHLOROFORM-d) 1.11 (s, 6 H) 2.31 (s, 3 H) 2.72 (s, 3 H) 2.81 (s, 2 H) 3.11 (s, 3 H) 4.09 (s, 2 H) 9.22 (brs, 1 H) |
| 77 | — | 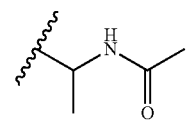 [SMILES: *C(C)NC(C)=O] | (200 MHz, DMSO-$d_6$) 1.44 (d, J = 7.0 Hz, 3 H) 1.86 (s, 3 H) 2.20 (s, 3 H) 2.65 (s, 3 H) 4.98-5.16 (m, 1 H) 8.50 (d, J = 7.9 Hz, 1 H) 12.70 (brs, 1 H) |

TABLE 8

| Example | Y | R3 | ¹H NMR (d ppm) |
|---|---|---|---|
| 78 | 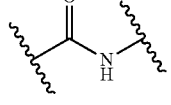 |  | (600 MHz, DMSO-$d_6$) 2.21 (s, 3 H) 2.69 (s, 3 H) 2.81 (d, J = 4.6 Hz, 3 H) 8.90 (d, J = 4.6 Hz, 1 H) 12.73 (brs, 1 H) |
| 79 | — | 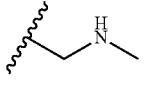 [SMILES: *CNC] | (600 MHz, DMSO-$d_6$) 2.20 (s, 3 H) 2.31 (s, 3 H) 2.65 (s, 3 H) 3.77 (s, 2 H) |
| 80 | — | 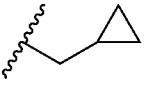 [SMILES: *CC1CC1] | (600 MHz, CHLOROFORM-d) 0.28-0.32 (m, 2 H) 0.57-0.61 (m, 2 H) 1.16-1.22 (m, 1 H) 2.31 (s, 3 H) 2.68 (d, J = 6.9 Hz, 2 H) 2.73 (s, 3H) 9.20 (brs, 1 H) |
| 81 | — | 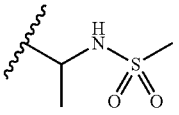 [SMILES: *C(C)NS(C)(=O)=O] | (600 MHz, DMSO-$d_6$) 1.51 (d, J = 6.9 Hz, 3 H) 2.20 (s, 3 H) 2.66 (s, 3 H) 2.96 (s, 3 H) 4.71-4.80 (m, 1 H) 7.94 (d, J = 7.8 Hz, 1H) 12.69 (brs, 1 H) |
| 82 | — | 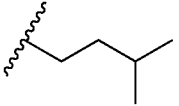 [SMILES: *CCC(C)C] | (200 MHz, CHLOROFORM-d) 0.98 (d, J = 7.0 Hz, 6 H) 1.61-1.77 (m, 2 H) 2.30 (s, 3 H) 2.66-2.82 (m, 2 H) 2.73 (s, 3 H) 9.79 (brs, 1 H) |
| 83 | — | 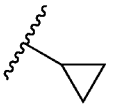 [SMILES: *C1CC1] | (600 MHz, DMSO-$d_6$) 0.94-0.97 (m, 2 H) 1.07-1.11 (m, 2 H) 2.12-2.17 (m, 1 H) 2.19 (s, 3 H) 2.61 (s, 3 H) 12.59 (brs, 1 H) |
| 84 | — | 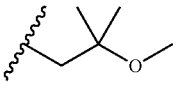 [SMILES: *CC(C)(C)OC] | (600 MHz, CHLOROFORM-d) 1.33 (s, 6 H) 2.30 (s, 3 H) 2.72 (s, 3 H) 2.98 (s, 2 H) 3.31 (s, 3 H) 9.17 (brs, 1 H) |

TABLE 8-continued

| Example | Y | R3 | ¹H NMR (d ppm) |
|---|---|---|---|
| 85 | — | (structure: CH2-C(CH3)2-CH(OH)-CH3) | (600 MHz, CHLOROFORM-d) 0.98 (s, 3 H) 1.03 (s, 3 H) 1.19 (d, J = 6.4 Hz, 3 H) 2.31 (s, 3 H) 2.67 (d, J = 13.7 Hz, 1 H) 2.71 (s, 3 H) 2.81 (brs, 1 H) 2.92 (d, J = 13.7 Hz, 1 H) 3.59 (m, 1 H) 9.39 (brs, 1 H) |
| 86 | — | (structure: CH2-C(CH3)2-C(=O)-CH3) | (200 MHz, CHLOROFORM-d) 1.27 (s, 6 H) 2.29 (s, 3 H) 2.31 (s, 3 H) 2.69 (s, 3 H) 3.03 (s, 2 H) |
| 87 | — | (morpholine N-linked) | (200 MHz, DMSO-d₆) 2.19 (s, 3 H) 2.62 (s, 3 H) 3.30-3.42 (m, 4 H) 3.64-3.76 (m, 4 H) 12.62 (brs, 1 H) |
| 88 | C(=O) | tert-butyl-CH2 | (200 MHz, CHLOROFORM-d) 1.42 (s, 9 H) 2.32 (s, 3 H) 2.77 (s, 3 H) 9.43 (brs, 1 H) |

TABLE 9

| Example | Y | R3 | ¹H NMR (d ppm) |
|---|---|---|---|
| 89 | — | (3-(2-oxopyrrolidin-1-yl)propyl) | (200 MHz, CHLOROFORM-d) 2.12 (m, 2 H) 2.22-2.26 (m, 2 H) 2.52-2.64 (m, 2 H) 2.59 (s, 3 H) 2.99 (t, J = 6.8 Hz, 2 H) 3.55 (t, J = 6.8 Hz, 2 H) 3.77 (t, J = 6.8 Hz, 2 H) 10.73 (brs, 1 H) |
| 90 | C(=O) | (3-hydroxyazetidin-1-yl) | (600 MHz, DMSO-d₆) 2.21 (s, 3 H) 2.67 (s, 3 H) 3.79-3.84 (m, 1 H) 4.17-4.22 (m, 1 H) 4.28-4.33 (m, 1 H) 4.51-4.57 (m, 1 H) 4.64-4.69 (m, 1 H) 5.84 (d, J = 6.4 Hz, 1 H) 12.73 (brs, 1 H) |
| 91 | C(=O)NH | CH2-CH(OH)-CH3 | (600 MHz, DMSO-d₆) 1.07 (d, J = 6.4 Hz, 3 H) 2.21 (s, 3 H) 2.69 (s, 3 H) 3.18-3.27 (m, 2 H) 3.72-3.87 (m, 1 H) 4.81 (d, J = 5.0 Hz, 1 H) 8.76 (t, J = 6.0 Hz, 1 H) 12.74 (brs, 1 H) |
| 92 | — | (tetrahydrofuran-2-yl) | (600 MHz, DMSO-d₆) 1.92-2.01 (m, 1 H) 2.02-2.15 (m, 2 H) 2.20 (s, 3 H) 2.24-2.33 (m, 1 H) 2.65 (s, 3 H) 3.82-3.89 (m, 1 H) 3.90-3.96 (m, 1 H) 5.07 (dd, J = 7.8, 5.5 Hz, 1 H) 12.68 (brs, 1 H) |
| 93 | — | (3-hydroxypiperidin-1-yl) | (600 MHz, DMSO-d₆) 1.31-1.41 (m, 1 H) 1.43-1.53 (m, 1 H) 1.71-1.79 (m, 1 H) 1.83-1.90 (m, 1 H) 2.19 (s, 3 H) 2.61 (s, 3 H) 2.83 (dd, J = 12.4, 8.7 Hz, 1 H) 2.94-3.03 (m, 1 H) 3.51-3.65 (m, 2 H) 3.78 (dd, J = 12.4, 4.1 Hz, 1 H) 4.93 (d, J = 4.1 Hz, 1 H) 12.61 (brs, 1 H) |
| 94 | — | (CH2-C(CH3)2-SO2-NH-tBu) | (600 MHz, CHLOROFORM-d) 1.41 (s, 9 H) 1.50 (s, 6 H) 2.31 (s, 3 H) 2.72 (s, 3 H) 3.24 (s, 2 H) 3.93 (brs, 1 H) 9.10 (brs, 1H) |
| 95 | — | (CH2-C(CH3)2-CH2F) | (600 MHz, CHLOROFORM-d) 1.07 (d, J = 1.8 Hz, 6 H) 2.31 (s, 3 H) 2.72 (s, 3 H) 2.72-2.88 (m, 2 H) 3.48-3.50 (brs, 1 H) 4.20-4.31 (m, 2 H) 8.92 (brs, 1 H) |

TABLE 9-continued

| Example | Y | R3 | $^1$H NMR (d ppm) |
|---|---|---|---|
| 96 | [amide -C(O)NH-] | [oxetanyl] | (600 MHz, DMSO-$d_6$) 2.21 (s, 3 H) 2.70 (s, 3 H) 4.66 (t, J = 6.4 Hz, 2 H) 4.75 (t, J = 7.1 Hz, 2 H) 4.96-5.08 (m, 1 H) 9.72 (d, J = 6.4 Hz, 1 H) 12.74 (brs, 1 H) |
| 97 | — | [2,2-dimethyl-3-hydroxypentyl] | (600 MHz, CHLOROFORM-d) 0.97 (s, 3 H) 1.00-1.04 (m, 6 H) 1.33-1.41 (m, 1 H) 2.31 (s, 3 H) 2.64 (d, J = 13.8 Hz, 1 H) 2.71 (s, 3 H) 2.94 (d, J = 14.2 Hz, 1 H) 3.18 (dd, J = 10.1, 4.6 Hz, 1 H) 9.08 (brs, 1 H) |
| 98 | — | [2-methyl-4-hydroxy-2-butenyl] | (200 MHz, CHLOROFORM-d) 2.21 (s, 3 H) 2.31 (s, 3 H) 2.74 (s, 3 H) 4.23-4.29 (m, 2 H) 6.50-6.57 (m, 1 H) |
| 99 | — | [pyrazol-1-ylmethyl] | (600 MHz, DMSO-$d_6$) 2.19 (s, 3 H) 2.62 (s, 3 H) 5.57 (s, 2 H) 6.26-6.36 (m, 1 H) 7.49 (d, J = 1.8 Hz, 1 H) 7.90 (d, J = 2.3 Hz, 1 H) 12.69 (brs, 1 H) |

TABLE 10

| Example | Y | R3 | $^1$H NMR (d ppm) |
|---|---|---|---|
| 100 | — | [2,2-dimethyl-3-hydroxy-3-phenylpropyl] | (600 MHz, CHLOROFORM-d) 0.97 (s, 3 H) 1.00 (s, 3 H) 2.30 (s, 3 H) 2.70-2.75 (m, 4 H) 3.02 (d, J = 14.2 Hz, 1 H) 3.08-3.13 (m, 1 H) 4.57 (d, J = 4.1 Hz, 1 H) 7.28 (d, J = 7.3 Hz, 1 H) 7.30-7.34 (m, 2 H) 7.35-7.38 (m, 2 H) 8.97 (brs, 1 H) |
| 101 | — | [2,2-dimethylcyclopropyl] | (600 MHz, CHLOROFORM-d) 1.03 (dd, J = 8.71, 4.6 Hz, 1 H) 1.15 (s, 3 H) 1.20-1.29 (m, 4 H) 1.93 (dd, J = 8.3, 5.5 Hz, 1 H) 2.30 (s, 3 H) 2.71 (s, 3 H) 9.29 (brs, 1 H) |
| 102 | — | [(3S)-3-hydroxypyrrolidin-1-yl] | (600 MHz, DMSO-$d_6$) 1.83-1.90 (m, 1 H) 1.95-2.04 (m, 1 H) 2.19 (s, 3 H) 2.62 (s, 3 H) 3.24-3.30 (m, 1 H) 3.39-3.49 (m, 3 H) 4.33-4.41 (m, 1H) |
| 103 | — | [(3R)-3-hydroxypyrrolidin-1-yl] | (600 MHz, DMSO-$d_6$) 1.83-1.90 (m, 1 H) 1.95-2.04 (m, 1 H) 2.19 (s, 3 H) 2.62 (s, 3 H) 3.24-3.30 (m, 1 H) 3.39-3.49 (m, 3 H) 4.33-4.41 (m, 1H) |
| 104 | — | [4-hydroxypiperidin-1-yl] | (200 MHz, CHLOROFORM-d) 1.67-2.05 (m, 4 H) 2.08 (s, 3 H) 2.30 (s, 3 H) 2.69 (s, 3 H) 3.26-3.45 (m, 2 H) 3.71-3.89 (m, 2 H) 4.91-5.07 (m, 1 H) 9.56 (brs, 1 H) |
| 105 | — | [ethyl 2,2-dimethyl-propanoate] | (200 MHz, CHLOROFORM-d) 1.29 (t, J = 7.2 Hz, 3 H) 1.32 (s, 6H) 2.30 (s, 3 H) 2.70 (s, 3 H) 3.06 (s, 2 H) 4.20 (q, J = 7.2 Hz, 3 H) 9.90 (brs, 1 H) |

TABLE 10-continued

| Example | Y | R3 | ¹H NMR (d ppm) |
|---|---|---|---|
| 106 | — | (structure: CH2-C(CH3)2-C(CH3)2-OH) | (600 MHz, CHLOROFORM-d) 1.06 (s, 6 H) 1.31 (s, 6 H) 2.32 (s, 3 H) 2.72 (s, 3 H) 2.88 (s, 2 H) 9.72 (brs, 1 H) |
| 107 | — | (structure: CH2-C(CH3)2-SO2NH2) | (600 MHz, CHLOROFORM-d) 1.56 (s, 6 H) 2.37 (s, 3 H) 2.75 (s, 3 H) 3.31 (s, 2 H) 4.61 (s, 2 H) |
| 108 | — | (structure: CH2-C(CH3)2-COOH) | (200 MHz, DMSO-$d_6$) 1.22 (s, 6 H) 2.20 (s, 3 H) 2.64 (s, 3 H) 2.96 (s, 2 H) 12.66 (s, 1 H) |
| 109 | — | (azetidine-3-ol, N-linked) | (200 MHz, CHLOROFORM-d) 2.12 (s, 3 H) 2.29 (s, 3 H) 2.68 (s, 3 H) 4.02-4.16 (m, 2 H) 4.38-4.51 (m, 2 H) 5.28-5.42 (m, 1 H) 9.63 (brs, 1 H) |
| 110 | — | (piperidin-3-ol, N-linked) | (200 MHz, CHLOROFORM-d) 1.67-2.00 (m, 4 H) 2.03 (s, 3 H) 2.29 (s, 3 H) 2.68 (s, 3 H) 3.41-3.58 (m, 3 H) 3.65-3.78 (m, 1 H) 4.86-5.00 (m, 1 H) 9.54 (brs, 1 H) |

TABLE 11

| Example | Y | R3 | ¹H NMR (d ppm) |
|---|---|---|---|
| 111 | — | (structure: CH2-C(CH3)2-CONH2) | (200 MHz, DMSO-$d_6$) 1.19 (s, 6 H) 2.19 (s, 3 H) 2.64 (s, 3 H) 2.92 (s, 2 H) 6.89 (brs, 1 H) 7.17 (brs, 1 H) |
| 112 | — | (tetrahydropyran-3-yl) | (600 MHz, CHLOROFORM-d) 1.74-1.80 (m, 2 H) 1.89-1.98 (m, 1 H) 2.18-2.24 (m, 1 H) 2.31 (s, 3 H) 2.71 (s, 3 H) 3.11-3.18 (m, 1 H) 3.51-3.57 (m, 1 H) 3.71 (dd, J = 11.0, 9.6 Hz, 1 H) 3.93-3.98 (m, 1 H) 4.14-4.19 (m, 1 H) 9.01 (brs, 1 H) |
| 113 | — | (2-oxo-1,2-dihydropyridin-4-yl) | (600 MHz, DMSO-$d_6$) 2.22 (s, 3 H) 2.71 (s, 3 H) 6.69 (d, J = 6.4 Hz, 1 H) 6.91-7.00 (m, 1 H) 7.58 (d, J = 6.4 Hz, 1 H) 11.95 (brs, 1 H) 12.72 (brs, 1 H) |

Hereinafter, Tables 12 to 17 show the structural formulae and the NMR values of Examples 114 to 176.

[Formula 7]

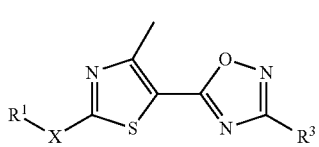

(3)

TABLE 12

| Example | R1 | X | R3 | ¹H NMR (d ppm) |
|---|---|---|---|---|
| 114 | H | NH | tert-butyl | (600 MHz, CHLOROFORM-d) 1.39 (s, 9 H) 2.62 (s, 3 H) 5.44 (brs, 2 H) |

TABLE 12-continued

| Example | R1 | X | R3 | $^1$H NMR (d ppm) |
|---|---|---|---|---|
| 115 | 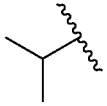 | 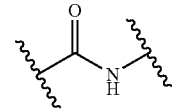 [SMILES: *NC(*)=O] | 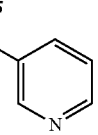 | (600 MHz, DMSO-d$_6$) 1.16 (d, J = 6.9 Hz, 6 H) 2.74 (s, 3 H) 2.79 (quin, J = 6.9 Hz, 1 H) 7.43-7.82 (m, 1 H) 8.27-8.53 (m, 1 H) 8.66-8.92 (m, 1 H) 9.07-9.31 (m, 1 H) 12.72 (brs, 1 H) |
| 116 | 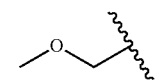 | 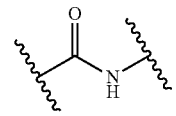 | 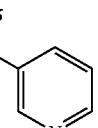 | (600 MHz, DMSO-d$_6$) 2.74 (s, 3 H) 3.38 (s, 3 H) 4.22 (s, 2 H) 7.50-7.79 (m, 1 H) 8.27-8.52 (m, 1 H) 8.71-8.90 (m, 1 H) 9.09-9.31 (m, 1 H) 12.74 (brs, 1 H) |
| 117 | 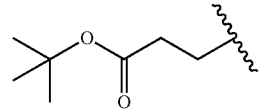 [SMILES: *CCC(=O)OC(C)(C)C] | 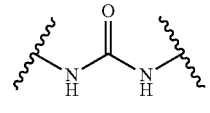 | 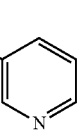 | (600 MHz, CHLOROFORM-d) 1.47 (s, 9 H) 2.55-2.59 (m, 2 H) 2.79 (s, 3 H) 3.63 (q, J = 5.8 Hz, 2 H) 7.34-7.58 (m, 1 H) 8.25-8.51 (m, 1 H) 8.61-8.88 (m, 1 H) 9.20-9.47 (m, 1 H) 9.70 (brs, 1 H) |
| 118 | 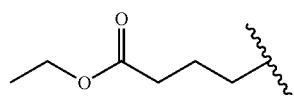 [SMILES: *CCCC(=O)OCC] | 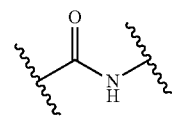 | 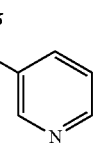 | (600 MHz, DMSO-d$_6$) 1.29 (t, J = 7.1 Hz, 3 H) 1.88 (quin, J = 7.3 Hz, 2 H) 2.37 (t, J = 7.3 Hz, 2 H) 2.55 (t, J = 7.3 Hz, 2 H) 2.73 (s, 3 H) 4.06 (q, J = 7.3 Hz, 2 H) 7.45-7.78 (m, 1 H) 8.25-8.51 (m, 1 H) 8.68-8.91 (m, 1 H) 9.08-9.33 (m, 1 H) 12.74 (brs, 1 H) |
| 119 | 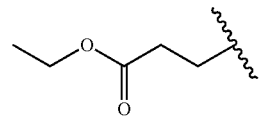 [SMILES: *CCC(=O)OCC] | 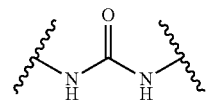 | 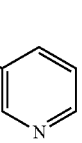 | (600 MHz, CHLOROFORM-d) 1.29 (t, J = 7.1 Hz, 3 H) 2.67 (t, J = 5.7 Hz, 2 H) 2.79 (s, 3 H) 3.54-3.76 (m, 2 H) 4.20 (q, J = 7.3 Hz, 2 H) 7.36-7.54 (m, 1 H) 8.31-8.46 (m, 1 H) 8.62-8.86 (m, 1 H) 9.26-9.41 (m, 1 H) 9.52 (brs, 1 H) |
| 120 | 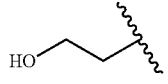 | 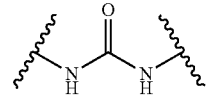 [SMILES: *NC(=O)N*] | 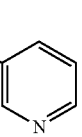 | (600 MHz, DMSO-d$_6$) 2.68 (s, 3 H) 3.24 (q, J = 5.7 Hz, 2 H) 3.49 (brs, 2 H) 4.83 (brs, 1 H) 6.80 (brs, 1 H) 7.51-7.71 (m, 1 H) 8.27-8.49 (m, 1 H) 8.68-8.87 (m, 1 H) 9.20-9.21 (m, 1 H) 11.08 (brs, 1 H) |
| 121 | 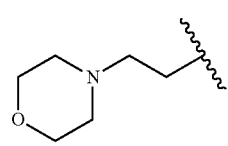 [SMILES: *CCN1CCOCC1] | 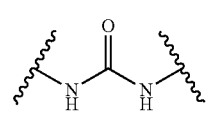 [SMILES: *NC(=O)N*] | 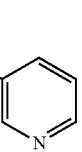 | (600 MHz, DMSO-d$_6$) 2.30-2.47 (m, 6 H) 2.68 (s, 3 H) 3.26-3.35 (m, 2 H) 3.59 (brs, 4 H) 6.72 (brs, 1 H) 7.44-7.72 (m, 1 H) 8.38-8.41 (m, 1 H) 8.66-8.91 (m, 1 H) 9.07-9.29 (m, 1 H) 11.24 (brs, 1 H) |
| 122 | 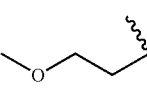 | 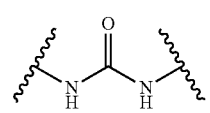 | 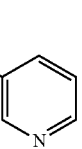 | (600 MHz, DMSO-d$_6$) 2.68 (s, 3 H) 3.29 (s, 3 H) 3.32-3.37 (m, 2 H) 3.43 (t, J = 5.5 Hz, 2 H) 6.82 (brs, 1 H) 7.53-7.73 (m, 1 H) 8.29-8.51 (m, 1 H) 8.68-8.90 (m, 1 H) 9.04-9.32 (m, 1 H) 11.07 (brs, 1 H) |

TABLE 12-continued

| Example | R1 | X | R3 | ¹H NMR (d ppm) |
|---|---|---|---|---|
| 123 | tert-butyl ester with alkyl chain | -NH-C(O)-NH- | tert-butyl | (600 MHz, CHLOROFORM-d) 1.40 (s, 9 H) 1.46 (s, 9 H) 2.55 (t, J = 5.7 Hz, 2 H) 2.71 (s, 3 H) 3.61 (q, J = 6.0 Hz, 2 H) 9.59 (brs, 1 H) |
| 124 | H | -NH-C(O)-NH- | 3-pyridyl | (600 MHz, DMSO-$d_6$) 2.68 (s, 3 H) 6.69 (brs, 2 H) 7.51-7.74 (m, 1 H) 8.23-8.52 (m, 1 H) 8.65-8.92 (m, 1 H) 9.08-9.32 (m, 1 H) 11.14 (brs, 1 H) |

TABLE 13

| Example | R1 | X | R3 | ¹H NMR (d ppm) |
|---|---|---|---|---|
| 125 | tert-butyl ester with alkyl chain | -NH-C(O)-NH- | 3-pyridyl | (600 MHz, CHLOROFORM-d) 1.46 (s, 9 H) 1.80-2.10 (m, 2 H) 2.38 (t, J = 7.1 Hz, 2 H) 2.80 (s, 3 H) 3.19-3.65 (m, 2 H) 7.34-7.59 (m, 1 H) 8.22-8.54 (m, 1 H) 8.64-8.90 (m, 1 H) 9.21-9.48 (m, 1 H) 9.95 (brs, 1 H) |
| 126 | tert-butyl ester with shorter alkyl chain | -NH-C(O)-NH- | 3-pyridyl | (600 MHz, CHLOROFORM-d) 1.52 (s, 9 H) 2.79 (s, 3 H) 4.07-4.12 (m, 2 H) 7.39-7.45 (m, 1 H) 8.33-8.40 (m, 1 H) 8.72-8.77 (m, 1 H) 9.31-9.36 (m, 1 H) |
| 127 | dimethylamino alkyl | -NH-C(O)-NH- | 3-pyridyl | (600 MHz, DMSO-$d_6$) 1.56 (quin, J = 6.8 Hz, 2 H) 2.10 (brs, 6 H) 2.21 (brs, 2 H) 2.63 (s, 3 H) 3.11-3.19 (m, 2 H) 6.85 (brs, 1 H) 7.53-7.62 (m, 1 H) 8.30-8.40 (m, 1 H) 8.72-8.79 (m, 1 H) 9.13-9.19 (m, 1 H) 11.20 (brs, 1 H) |
| 128 | methoxy alkyl | -C(O)-NH- | 3-pyridyl | (600 MHz, DMSO-$d_6$) 1.86 (quin, J = 6.9 Hz, 2 H) 2.55 (t, J = 7.6 Hz, 2 H) 2.73 (s, 3 H) 3.23 (s, 3 H) 3.36 (t, J = 6.2 Hz, 2 H) 7.60-7.67 (m, 1 H) 8.36-8.45 (m, 1 H) 8.76-8.84 (m, 1 H) 9.17-9.24 (m, 1 H) 12.73 (brs, 1 H) |
| 129 | tert-butyl ester with alkyl chain | -O-C(O)-NH- | 3-pyridyl | (600 MHz, CHLOROFORM-d) 1.46 (s, 9 H) 2.68 (t, J = 6.4 Hz, 2 H) 2.81 (s, 3 H) 4.57 (t, J = 6.2 Hz, 2 H) 7.40-7.49 (m, 1 H) 8.36-8.47 (m, 1 H) 8.72-8.80 (m, 1 H) 9.34-9.42 (m, 1 H) 9.82 (brs, 1 H) |
| 130 | tert-butoxy alkyl | -NH-C(O)-NH- | 3-pyridyl | (600 MHz, CHLOROFORM-d) 1.22 (s, 9 H) 1.84 (quin, J = 6.0 Hz, 2 H) 2.79 (s, 3 H) 3.48 (q, J = 5.7 Hz, 2 H) 3.53 (t, J = 5.5 Hz, 2 H) 7.40-7.49 (m, 1 H) 8.34-8.45 (m, 1 H) 8.72-8.80 (m, 1 H) 9.33-9.39 (m, 1 H) 9.56 (brs, 1 H) |

TABLE 13-continued

| Example | R1 | X | R3 | $^1$H NMR (d ppm) |
|---|---|---|---|---|
| 131 | (N,N-dimethyl butanamide) | urea linker | 3-pyridyl | (600 MHz, DMSO-d$_6$) 2.55 (t, J = 6.2 Hz, 2 H) 2.67 (s, 3 H) 2.85 (s, 3 H) 2.95 (s, 3 H) 3.36-3.41 (m, 2 H) 6.86-6.96 (m, 1 H) 7.58-7.67 (m, 1 H) 8.33-8.45 (m, 1 H) 8.73-8.86 (m, 1 H) 9.15-9.23 (m, 1 H) 11.10 (brs, 1 H) |
| 132 | (N-tert-butyl butanamide) | urea linker | 3-pyridyl | (600 MHz, DMSO-d$_6$) 1.26 (s, 9 H) 2.28 (t, J = 6.4 Hz, 2 H) 2.68 (s, 3 H) 3.30-3.36 (m, 2 H) 6.83 (brs, 1 H) 7.52 (brs, 1 H) 7.60-7.66 (m, 1 H) 8.37-8.43 (m, 1 H) 8.76-8.83 (m, 1 H) 9.18-9.22 (m, 1 H) 11.19 (brs, 1 H) |
| 133 | (N-tert-butyl propanesulfonamide) | urea linker | 3-pyridyl | (600 MHz, DMSO-d$_6$) 1.28 (s, 9 H) 2.69 (s, 3 H) 3.22 (t, J = 6.7 Hz, 2 H) 3.56 (q, J = 6.4 Hz, 2 H) 6.90 (brs, 1 H) 6.98 (s, 1 H) 7.59-7.67 (m, 1 H) 8.37-8.44 (m, 1 H) 8.77-8.83 (m, 1 H) 9.18-9.23 (m, 1 H) 11.52 (brs, 1 H) |
| 134 | (Boc-NH-propyl) | urea linker | 3-pyridyl | (600 MHz, DMSO-d$_6$) 1.38 (s, 9 H) 2.68 (s, 3 H) 2.98-3.09 (m, 2 H) 3.15-3.26 (m, 2 H) 6.77 (brs, 1 H) 6.86-6.95 (m, 1 H) 7.58-7.68 (m, 1 H) 8.36-8.44 (m, 1 H) 8.76-8.83 (m, 1 H) 9.17-9.24 (m, 1 H) |
| 135 | (pivaloyloxyethyl) | urea linker | 3-pyridyl | (600 MHz, CHLOROFORM-d) 1.23 (s, 9 H) 2.80 (s, 3 H) 3.68 (q, J = 5.5 Hz, 2 H) 4.29 (t, J = 5.5 Hz, 2 H) 7.39-7.50 (m, 1 H) 8.36-8.45 (m, 1 H) 8.71-8.87 (m, 1 H) 9.30-9.44 (m, 1 H) 9.81 (brs, 1 H) |

TABLE 14

| Example | R1 | X | R3 | $^1$H NMR (d ppm) |
|---|---|---|---|---|
| 136 | (HOOC-propyl) | urea linker | 3-pyridyl | (600 MHz, DMSO-d$_6$) 2.41-2.54 (m, 2 H) 2.68 (s, 3 H) 3.29-3.46 (m, 2 H) 4.28 (brs, 1 H) 6.86-6.99 (m, 1 H) 7.63-7.74 (m, 1 H) 8.41-8.51 (m, 1 H) 8.78-8.87 (m, 1 H) 9.18-9.27 (m, 1 H) 11.18 (brs, 1 H) |
| 137 | (4-hydroxypiperidinyl) | amide linker | 3-pyridyl | (660 MHz, DMSO-d$_6$) 1.27-1.40 (m, 2 H) 1.67-1.82 (m, 2 H) 2.70 (s, 3 H) 3.13-3.24 (m, 2 H) 3.63-3.76 (m, 1 H) 3.82-3.96 (m, 2 H) 4.74 (d, J = 4.1 Hz, 1 H) 7.57-7.67 (m, 1 H) 8.35-8.46 (m, 1 H) 8.75-8.85 (m, 1 H) 9.15-9.25 (m, 1 H) 11.68 (brs, 1H) |

TABLE 14-continued

| Example | R1 | X | R3 | ¹H NMR (d ppm) |
|---|---|---|---|---|
| 138 | H₂N-(CH₂)₃- | -NH-C(O)-NH- | 3-pyridyl | (600 MHz, DMSO-d₆) 2.58-2.79 (m, 5 H) 3.14-3.24 (m, 2 H) 6.89 (brs, 1 H) 7.58-7.66 (m, 1 H) 8.35-8.42 (m, 1 H) 8.74-8.82 (m, 1 H) 9.16-9.22 (m, 1 H) |
| 139 | (CH₃)₃C-C(O)-NH-(CH₂)₃- | -NH-C(O)-NH- | 3-pyridyl | (600 MHz, DMSO-d₆) 1.08 (s, 9 H) 2.68 (s, 3 H) 3.13-3.21 (m, 2 H) 3.22-3.28 (m, 2 H) 6.70 (brs, 1 H) 7.56 (t, J = 5.3 Hz, 1 H) 7.60-7.66 (m, 1 H) 8.34-8.45 (m, 1 H) 8.73-8.84 (m, 1 H) 9.15-9.24 (m, 1 H) 11.30 (brs, 1H) |
| 140 | iPrO-C(O)-(CH₂)₃- | -NH-C(O)-NH- | 3-pyridyl | (600 MHz, DMSO-d₆) 1.15 (d, J = 6.0 Hz, 6 H) 2.62-2.78 (m, 2 H) 2.74 (s, 3 H) 3.19-3.40 (m, 2 H) 4.73 (dt, J = 12.5, 6.4 Hz, 1 H) 7.06-7.17 (m, 1 H) 7.57-7.70 (m, 1 H) 8.34-8.46 (m, 1 H) 8.74-8.87 (m, 1 H) 9.13-9.26 (m, 1 H) 12.75 (brs, 1 H) |
| 141 | tBuO-C(O)-(CH₂)₃- | -NH-C(O)-NH- | 5-pyrimidyl | (600 MHz, DMSO-d₆) 1.42 (s, 9 H) 2.45 (t, J = 6.4 Hz, 2 H) 2.69 (s, 3 H) 3.37 (q, J = 6.1 Hz, 2 H) 6.78-6.83 (m, 1 H) 9.39 (s, 2 H) 9.42 (s, 1 H) 11.27 (brs, 1 H) |
| 142 | morpholino-(CH₂)₄- | -NH-C(O)-NH- | 3-pyridyl | (600 MHz, DMSO-d₆) 1.63 (quin, J = 7.0 Hz, 2 H) 2.26-2.42 (m, 6 H) 2.68 (s, 3 H) 3.15-3.25 (m, 2 H) 3.59 (brs, 4 H) 6.77 (brs, 1 H) 7.57-7.69 (m, 1 H) 8.34-8.43 (m, 1 H) 8.75-8.86 (m, 1 H) 9.14-9.26 (m, 1 H) 11.22 (brs, 1 H) |
| 143 | EtO-C(O)-CH₂-CH(CH₃)- | -NH-C(O)-NH- | 3-pyridyl | (600 MHz, DMSO-d₆) 1.13-1.23 (m, 6 H) 2.52-2.61 (m, 2 H) 2.68 (s, 3 H) 3.98-4.19 (m, 3 H) 6.69-6.84 (m, 1 H) 7.56-7.69 (m, 1 H) 8.35-8.46 (m, 1 H) 8.74-8.86 (m, 1 H) 9.16-9.25 (m, 1 H) 11.08 (brs, 1 H) |
| 144 | 2-(ethoxycarbonyl)cyclopentyl | -NH-C(O)-NH- | 3-pyridyl | (600 MHz, DMSO-d₆) 1.12 (t, J = 7.1 Hz, 3 H) 1.52-2.02 (m, 6 H) 2.68 (s, 3 H) 3.01 (q, J = 7.5 Hz, 1 H) 3.93-4.12 (m, 2 H) 4.32-4.43 (m, 1 H) 6.67 (brs, 1 H) 7.55-7.69 (m, 1 H) 8.34-8.45 (m, 1 H) 8.75-8.84 (m, 1 H) 9.16-9.24 (m, 1 H) 10.85 (brs, 1H) |
| 145 | morpholino-C(O)-(CH₂)₃- | -NH-C(O)-NH- | 3-pyridyl | (600 MHz, DMSO-d₆) 2.57 (t, J = 6.2 Hz, 2 H) 2.67 (s, 3 H) 3.35-3.60 (m, 10 H) 6.81-6.97 (m, 1 H) 7.57-7.69 (m, 1 H) 8.34-8.45 (m, 1 H) 8.72-8.83 (m, 1 H) 9.14-9.25 (m, 1 H) 11.17 (brs, 1 H) |

TABLE 14-continued

| Example | R1 | X | R3 | $^1$H NMR (d ppm) |
|---|---|---|---|---|
| 146 | H | —NH— | —CH$_2$CF$_3$ | (600 MHz, DMSO-d$_6$) 2.50 (s, 3 H) 4.02 (q, J = 10.7 Hz, 2 H) 8.06 (s, 2 H) |

TABLE 15

| Example | R1 | X | R3 | $^1$H NMR (d ppm) |
|---|---|---|---|---|
| 147 | tert-butyl ester-(CH$_2$)$_3$- | —NHC(O)NH— | —CH$_2$CF$_3$ | (600 MHz, CHLOROFORM-d) 1.46 (s, 9 H) 2.53-2.57 (m, 2 H) 2.73 (s, 3 H) 3.56-3.68 (m, 4 H) 9.54 (brs, 1 H) |
| 148 | tert-butylamino-(CH$_2$)$_3$- | —NHC(O)NH— | 3-pyridyl | (600 MHz, DMSO-d$_6$) 1.12 (brs, 9 H) 1.64 (brs, 2 H) 2.64 (brs, 3 H) 3.10-3.28 (m, 4 H) 6.19 (brs, 1 H) 7.00 (brs, 1 H) 7.56-7.67 (m, 1 H) 8.33-8.42 (m, 1 H) 8.73-8.83 (m, 1 H) 9.14-9.23 (m, 1 H) |
| 149 | HOCH$_2$C(CH$_3$)$_2$NHC(O)(CH$_2$)$_2$- | —NHC(O)NH— | 3-pyridyl | (600 MHz, DMSO-d$_6$) 1.19 (s, 6 H) 2.31 (t, J = 6.4 Hz, 2 H) 2.68 (s, 3 H) 3.32-3.36 (m, 2 H) 3.39 (brs, 2 H) 4.81 (brs, 1 H) 6.82 (brs, 1 H) 7.39 (s, 1 H) 7.56-7.69 (m, 1 H) 8.34-8.45 (m, 1 H) 8.73-8.85 (m, 1 H) 9.16-9.25 (m, 1 H) 11.19 (brs, 1 H) |
| 150 | 4-hydroxypiperidinyl-C(O)(CH$_2$)$_2$- | —NHC(O)NH— | 3-pyridyl | (600 MHz, DMSO-d$_6$) 1.19-1.38 (m, 2 H) 1.63-1.78 (m, 2 H) 2.52-2.60 (m, 2 H) 2.67 (s, 3 H) 2.96-3.08 (m, 1 H) 3.09-3.19 (m, 1 H) 3.38 (q, J = 6.0 Hz, 2 H) 3.59-3.74 (m, 2 H) 3.87-3.98 (m, 1 H) 4.73 (d, J = 4.1 Hz, 1 H) 6.83 (brs, 1 H) 7.56-7.68 (m, 1 H) 8.36-8.44 (m, 1 H) 8.75-8.84 (m, 1 H) 9.14-9.25 (m, 1 H) 11.14 (brs, 1 H) |
| 151 | HOCH$_2$CH$_2$OC(O)(CH$_2$)$_2$- | —NHC(O)NH— | 3-pyridyl | (600 MHz, DMSO-d$_6$) 2.67 (t, J = 6.9 Hz, 2H) 2.74 (s, 3 H) 3.30-3.35 (m, 2 H) 3.44-3.60 (m, 2 H) 3.95 (t, J = 5.3 Hz, 2 H) 4.70 (t, J = 5.3 Hz, 1 H) 7.18-7.31 (m, 1 H) 7.56-7.69 (m, 1 H) 8.33-8.48 (m, 1 H) 8.73-8.86 (m, 1 H) 9.16-9.27 (m, 1 H) 12.77 (brs, 1 H) |
| 152 | (HOCH$_2$)$_2$C(CH$_3$)NHC(O)(CH$_2$)$_2$- | —NHC(O)NH— | 3-pyridyl | (600 MHz, DMSO-d$_6$) 1.14 (s, 3 H) 2.35 (t, J = 6.4 Hz, 2 H) 2.68 (s, 3 H) 3.33-3.38 (m, 2H) 3.40-3.53 (m, 4 H) 4.73 (brs, 2 H) 6.81 (brs, 1 H) 7.29 (brs, 1 H) 7.59-7.67 (m, 1 H) 8.36-8.43 (m, 1 H) 8.76-8.83 (m, 1 H) 9.17-9.23 (m, 1 H) |
| 153 | tert-butyl ester-(CH$_2$)$_3$- | —NHC(O)NH— | cyclohexyl | (200 MHz, CHLOROFORM-d) 1.46 (s, 3 H) 1.25-2.08 (m, 10 H) 2.71 (s, 3 H) 2.69-2.92 (m, 1 H) 3.52-3.70 (m, 2 H) 7.27 (brs, 1H) 10.39 (brs, 1 H) |

TABLE 15-continued

| Example | R1 | X | R3 | ¹H NMR (d ppm) |
|---|---|---|---|---|
| 154 | tert-butyl ester with butyl chain | -NH-C(O)-NH- | -CH2CH2-O-CH3 | (200 MHz, CHLOROFORM-d) 1.46 (s, 9 H) 2.55 (t, J = 6.0 Hz, 2 H) 2.71 (s, 3 H) 3.04 (t, J = 6.6 Hz, 2 H) 3.39 (s, 3 H) 3.62 (q, J = 6.0 Hz, 2 H) 3.82 (t, J = 6.6 Hz, 2 H) 7.43 (brs, 1 H) 10.05 (brs, 1 H) |
| 155 | tris(hydroxymethyl)methyl amide with propyl chain | -NH-C(O)-NH- | pyridin-3-yl | (600 MHz, DMSO-d₆) 2.22 (s, 3 H) 2.73 (s, 3 H) 4.59 (s, 2 H) 5.36 (t, J = 5.7 Hz, 1 H) 7.53 (d, J = 8.3 Hz, 2 H) 7.98-8.05 (m, 2 H) 12.71 (brs, 1 H) |
| 156 | H | -NH- | -CH2-C(CH3)2-CH2-OH | (600 MHz, DMSO-d₆) 0.88 (s, 6 H) 2.49 (s, 3 H) 2.58 (s, 2 H) 3.21 (d, J = 5.5 Hz, 2 H) 4.66 (t, J = 5.5 Hz, 1 H) |
| 157 | tert-butyl ester with butyl chain | -NH-C(O)-NH- | -CH2-C(CH3)2-CH2-OH | (600 MHz, CHLOROFORM-d) 1.01 (s, 6 H) 1.46 (s, 9 H) 2.55 (t, J = 6.0 Hz, 2 H) 2.70 (s, 3 H) 2.75 (s, 2 H) 2.83 (t, J = 6.0 Hz, 1 H) 3.34-3.40 (m, 3 H) 3.58-3.63 (m, 2 H) 9.37 (brs, 1 H) |

TABLE 16

| Example | R1 | X | R3 | ¹H NMR (d ppm) |
|---|---|---|---|---|
| 158 | ethyl | -O-C(O)-NH- | -CH2-C(CH3)2-CH2-OH | (600 MHz, CHLOROFORM-d) 1.02 (s, 6 H) 1.38 (t, J = 7.2 Hz, 3 H) 2.73 (s, 3 H) 2.76 (s, 2 H) 3.38 (d, J = 6.9 Hz, 2 H) 4.37 (q, J = 7.2 Hz, 2 H) 9.79 (brs, 1 H) |
| 159 | 2-oxopyrrolidin-1-yl propyl | -NH-C(O)-NH- | -CH2-C(CH3)2-CH2-OH | (600 MHz, CHLOROFORM-d) 1.01 (s, 6 H) 1.81 (s, 2 H) 2.04-2.12 (m, 2 H) 2.48-2.53 (m, 2 H) 2.64 (s, 3 H) 2.73 (s, 2 H) 3.30-3.35 (m, 2 H) 3.35-3.38 (m, 2 H) 3.42-3.47 (m, 4 H) 6.98 (brs, 1 H) |
| 160 | tert-butoxy propyl | -NH-C(O)-NH- | -CH2-C(CH3)2-CH2-OH | (600 MHz, CHLOROFORM-d) 1.01 (s, 6 H) 1.21 (s, 9 H) 1.78-1.84 (m, 2 H) 2.69 (s, 3 H) 2.75 (s, 2 H) 3.37 (s, 2 H) 3.43-3.48 (m, 2 H) 3.51 (t, J = 5.7 Hz, 2 H) |
| 161 | tert-butylamide with propyl chain | -NH-C(O)-NH- | -CH2-C(CH3)2-CH2-OH | (600 MHz, CHLOROFORM-d) 1.02 (s, 6 H) 1.35 (s, 9 H) 2.50 (t, J = 5.7 Hz, 2 H) 2.64 (s, 3 H) 2.74 (s, 2 H) 3.10 (brs, 1 H) 3.39 (s, 2 H) 3.60 (q, J = 6.0 Hz, 2 H) 5.73 (s, 1 H) |
| 162 | 1-isopropylimidazol-4-yl propyl | -NH-C(O)-NH- | -CH2-C(CH3)2-CH2-OH | (600 MHz, CHLOROFORM-d) 1.01 (s, 6 H) 1.46 (d, J = 6.9 Hz, 6 H) 2.64 (s, 3 H) 2.73 (s, 2 H) 2.81 (t, J = 6.2 Hz, 2 H) 3.37 (s, 2 H) 3.55-3.67 (m, 2 H) 4.23-4.33 (m, 1 H) 6.79 (s, 1 H) 7.46 (s, 1 H) |
| 163 | Boc-NH-ethyl | -C(O)-NH- | -CH2-C(CH3)2-CH2-OH | (600 MHz, CHLOROFORM-d) 1.02 (s, 6 H) 1.45 (s, 9 H) 2.71 (s, 3 H) 2.76 (brs, 4 H) 3.38 (brs, 2 H) 3.50-3.59 (m, 2 H) 5.10 (brs, 1 H) 9.61 (brs, 1 H) |

TABLE 16-continued

| Example | R1 | X | R3 | ¹H NMR (d ppm) |
|---|---|---|---|---|
| 164 | HO–C(CH₃)(CH₂OH)–NH–C(O)–CH₂CH₂– (structure) | –NH–C(O)–NH– | –CH₂–CF₂–F | (600 MHz, DMSO-d₆) 1.14 (s, 3 H) 2.34 (t, J = 6.4 Hz, 2 H) 2.60 (s, 3 H) 3.29-3.37 (m, 2 H) 3.40-3.52 (m, 4 H) 4.08 (q, J = 10.7 Hz, 2 H) 4.73 (brs, 2 H) 6.80 (brs, 1 H) 7.27 (s, 1 H) 11.17 (brs, 1 H) |
| 165 | tBuO–C(O)–CH₂CH₂CH₂– (structure) | –NH–C(O)–NH– | –CH₂–S(O)₂–CH₃ | (200 MHz, DMSO-d₆) 2.39-2.52 (m, 2 H) 2.62 (s, 3 H) 3.21 (s, 3 H) 3.38 (m., 2 H) 4.87 (s, 2 H) 6.79 (brs, 1 H) 11.22 (brs, 1H) |
| 166 | 4-hydroxypiperidine-N–C(O)–CH₂CH₂– (structure) | –NH–C(O)–NH– | –CH₂–CF₂–F | (600 MHz, DMSO-d₆) 1.19-1.36 (m, 2 H) 1.64-1.76 (m, 2 H) 2.52-2.57 (m, 2 H) 2.60 (s, 3 H) 2.99-3.07 (m, 1 H) 3.09-3.17 (m, 1 H) 3.34-3.41 (m, 2 H) 3.60-3.72 (m, 2 H) 3.88-3.96 (m, 1 H) 4.08 (q, J = 10.9 Hz, 2 H) 4.73 (d, J = 4.1 Hz, 1 H) 6.79-6.98 (m, 1 H) 11.10 (brs, 1 H) |
| 167 | CH₃O–CH₂CH₂–NH–C(O)–CH₂CH₂– (structure) | –NH–C(O)–NH– | –CH₂–CF₂–F | (600 MHz, DMSO-d₆) 2.33 (t, J = 6.4 Hz, 2 H) 2.60 (s, 3 H) 3.20-3.26 (m, 5 H) 3.30-3.38 (m, 4 H) 4.08 (q, J = 10.9 Hz, 2 H) 6.87 (brs, 1 H) 8.01 (t, J = 5.7 Hz, 1 H) 11.11 (brs, 1 H) |
| 168 | Boc-piperazine-N–C(O)–CH₂CH₂– (structure) | –NH–C(O)–NH– | –CH₂–CF₂–F | (600 MHz, DMSO-d₆) 1.40 (s, 9 H) 2.57 (t, J = 6.0 Hz, 2 H) 2.60 (s, 3 H) 3.26-3.49 (m, 10 H) 4.08 (q, J = 10.6 Hz, 2 H) 6.88 (brs, 1 H) 11.14 (brs, 1 H) |

TABLE 17

| Example | R1 | X | R3 | ¹H NMR (d ppm) |
|---|---|---|---|---|
| 169 | piperazine-N–C(O)–CH₂CH₂– (structure) | –NH–C(O)–NH– | –CH₂–CF₂–F | (600 MHz, DMSO-d₆) 2.51-2.55 (m, 2 H) 2.60 (s, 3 H) 2.62-2.70 (m, 4 H) 3.24-3.43 (m, 6 H) 4.08 (q, J = 10.9 Hz, 2 H) 6.89 (t, J = 5.1 Hz, 1 H) |
| 170 | tBuO–C(O)–CH₂CH₂CH₂– (structure) | –NH–C(O)–NH– | –C(CH₃)₂–CH₂–OH | (200 MHz, CHLOROFORM-d) 1.33 (s, 6 H) 1.45 (s, 9 H) 2.48-2.60 (m, 2 H) 2.69 (s, 3 H) 2.96 (s, 2 H) 3.53-3.66 (m, 2 H) 7.13 (brs, 2 H) 7.73 (brs, 1 H) |
| 171 | 2-pyridyl–CH₂CH₂– (structure) | –NH–C(O)–NH– | 3-pyridyl–CH₂– (structure) | (600 MHz, DMSO-d₆) 2.67 (s, 3 H) 2.97 (t, J = 7.1 Hz, 2 H) 3.52-3.62 (m, 2 H) 6.86 (brs, 1 H) 7.22-7.27 (m, 1 H) 7.28-7.33 (m, 1 H) 7.60-7.66 (m, 1 H) 7.70-7.77 (m, 1 H) 8.43 (s, 1 H) 8.50-8.55 (m, 1 H) 8.75-8.85 (m, 1 H) 9.20 (d, J = 16.5 Hz, 1H) 11.19 (brs, 1H) |

TABLE 17-continued

| Example | R1 | X | R3 | $^1$H NMR (d ppm) |
|---|---|---|---|---|
| 172 | 1-ethylimidazol-4-yl-ethyl | –NH–C(O)–NH– | pyridin-3-yl | (600 MHz, CHLOROFORM-d) 1.46 (t, J = 7.3 Hz, 3 H) 2.75 (s, 2 H) 2.80-2.85 (m, 1 H) 3.62 (brs, 1 H) 3.97 (q, J = 7.3 Hz, 1 H) 6.77 (s, 1 H) 7.42-7.44 (m, 1 H) 7.48 (s, 1 H) 8.38-8.40 (m, 1 H) 8.74-8.75 (m, 1 H) 9.35 (m, 1 H) |
| 173 | methoxymethyl | –C(O)–NH– | 3-(hydroxymethyl)phenyl | (200 MHz, DMSO-$d_6$) 2.74 (s, 3 H) 3.32 (s, 3 H) 4.23 (s, 2 H) 4.61 (d, J = 5.5 Hz, 2 H) 5.38 (t, J = 5.5 Hz, 1 H) 7.54 (m, 2 H) 7.86-7.98 (m, 1 H) 8.00-8.07 (m, 1 H) 12.71 (brs, 1 H) |
| 174 | 3-hydroxybutyl | –NH–C(O)–NH– | 3-hydroxyphenyl | (600 MHz, DMSO-$d_6$) 1.06 (d, J = 6.0 Hz, 3 H) 2.66 (s, 3 H) 2.98-3.04 (m, 1 H) 3.19-3.25 (m, 1 H) 3.68-3.76 (m, 1 H) 4.82-4.88 (m, 1 H) 6.73-6.80 (m, 1 H) 6.95-7.00 (m, 1 H) 7.37 (t, J = 7.8 Hz, 1 H) 7.44-7.49 (m, 2 H) 9.84 (s, 1 H) 10.99 (brs, 1H) |
| 175 | 3-hydroxybutyl | –NH–C(O)–NH– | pyridin-3-yl | (600 MHz, DMSO-$d_6$) 1.07 (d, J = 6.4 Hz, 3 H) 2.68 (s, 3 H) 2.98-3.05 (m, 1 H) 3.19-3.26 (m, 1 H) 3.70-3.74 (m, 1 H) 4.86 (brd, J = 4.1 Hz, 1 H) 6.75-6.79 (m, 1 H) 7.62-7.64 (m, 1 H) 8.38-8.41 (m, 1 H) 8.79-8.81 (m, 1 H) 9.20-9.21 (m, 1 H) 10.94 (brs, 1 H) |
| 176 | 3-hydroxybutyl | –NH–C(O)–NH– | pyrimidin-5-yl | (600 MHz, DMSO-$d_6$) 1.06 (d, J = 6.0 Hz, 3 H) 2.68 (s, 3 H) 2.99-3.04 (m, 1 H) 3.19-3.24 (m, 1 H) 3.72 (brs, 1 H) 4.84-4.87 (m, 1 H) 6.77 (brs, 1 H) 9.38 (s, 2 H) 9.42 (s, 1 H) |

Test Example 1

PI 3-kinase p120γ Enzyme Activity Inhibition Test

Using human PI 3-kinase p120γ (manufactured by Millipore Corporation) and a mixed micellized product (hereinafter abbreviated as PIP$_2$-PS) of the substrate thereof, L-a-Phosphatidyl-D-myo-inositol-4,5-bisphosphate (product of Calbiochem, hereinafter abbreviated as PIP$_2$), and L-a-Phosphatidyl-L-Serine (manufactured by Sigma, hereinafter abbreviated as PS), the compound of the present invention was examined for the inhibitory action on PI3 Kinase p120γ enzyme activity (Km=8.9 μM for ATP, Km=4.0 μM for PIP$_2$-PS).

PIP$_2$-PS was prepared by mixing 500 μM of PIP$_2$ and 2.5 nM of PS and sonicating the mixture for 40 minutes while ice cooling to cause micellization. ATP (final concentration 10.0 μM), [γ-$^{33}$P] ATP (final concentration 10 μCi/ml), PIP$_2$-PS (final concentration 5.0 μM) and DMSO solutions of the test compound in different concentrations (compound final concentration $1.0 \times 10^{-5}$ to $2.4 \times 10^{-12}$ M, DMSO final concentration 0.1%) were added to PI 3-kinase p120γ, stirred and reacted at 30° C. for 2 hours. Using Phospholipid-Coated FlashPlate Microplates, 96-Well and Phospholipid Flash-Plate Coating Buffer (both manufactured by PerkinElmer Co., Ltd.), PIP$_2$-PS and phosphorylated PIP$_2$-PS were allowed to be adsorbed to the well wall of the plate and collected. The well was washed twice with PBS (Phosphate-Buffered Saline) and dried. The radioactivity was measured using Top Count NXT (manufactured by PerkinElmer Co., Ltd.), whereby the phosphorylated amount (a) of PIP$_2$-PS at the time of compound addition was calculated.

The same procedure was carried out in the absence of the test compound and the phosphorylated amount (b) of PIP$_2$-PS was calculated. Further, the same procedure was carried out in the absence of both of the substrate and the test compound, and the PIP$_2$-PS phosphorylated amount (c) of the background was calculated.

The PI3 Kinase p120γ enzyme activity suppression rate of the compound was calculated by the following formula.

Suppression rate (%)=[1−(a−c)/(b−c)]×100

Further, the activity of the test compound was calculated as the value which exhibits 50% radioactivity relative to the non-addition group (IC$_{50}$ value). More specifically, using the suppression rate by the test compound of different concentrations, the IC$_{50}$ value was calculated according to the dose-dependent inhibition curve analyzed by a data analysis software Origin (Lightstone Corp.) and used as the inhibitory activity index. Tables 18 and 19 show the results. In Tables 18 and 19, A indicates an $IC_{50}$ value of below 100 nM, B indicates an $IC_{50}$ value of 100 nM or more and below 500 nM, and C indicates an $IC_{50}$ value of 500 nM or more and 10 μM or less. An example of A is Example 82 ($IC_{50}$ value; 88 nM), an example of B is Example 67 ($IC_{50}$ value; 428 nM) and an example of C is Example 5 ($IC_{50}$ value; 7230 nM).

TABLE 18

| Example | PI3Kγ |
|---|---|
| 1 | A |
| 2 | A |
| 3 | A |
| 4 | A |
| 5 | C |
| 6 | A |
| 7 | A |
| 8 | C |
| 9 | A |
| 10 | B |
| 11 | C |
| 12 | B |
| 13 | B |
| 14 | A |
| 15 | A |
| 16 | A |
| 17 | A |
| 18 | A |
| 19 | A |
| 20 | A |
| 21 | A |
| 22 | B |
| 23 | A |
| 24 | A |
| 25 | A |
| 26 | A |
| 27 | A |
| 28 | A |
| 29 | A |
| 30 | C |
| 31 | A |
| 32 | A |
| 33 | B |
| 34 | A |
| 35 | B |
| 36 | C |
| 37 | A |
| 38 | B |
| 39 | B |
| 40 | B |
| 41 | A |
| 42 | A |
| 43 | C |
| 44 | A |
| 45 | B |
| 46 | A |
| 47 | B |
| 48 | A |
| 49 | B |
| 50 | B |
| 51 | A |
| 52 | C |
| 53 | A |
| 54 | A |
| 55 | B |
| 56 | C |
| 57 | B |
| 58 | C |
| 59 | C |
| 60 | A |
| 61 | B |
| 62 | A |
| 63 | A |
| 64 | A |
| 65 | A |
| 66 | B |
| 67 | B |

TABLE 18-continued

| Example | PI3Kγ |
|---|---|
| 68 | A |
| 69 | A |
| 70 | B |
| 71 | B |
| 72 | C |
| 73 | A |
| 74 | C |
| 75 | C |
| 76 | B |
| 77 | C |
| 78 | B |
| 79 | C |
| 80 | A |
| 81 | C |
| 82 | A |
| 83 | A |
| 84 | B |
| 85 | A |
| 86 | A |
| 87 | B |
| 88 | B |
| 89 | C |
| 90 | B |
| 91 | B |
| 92 | B |
| 93 | A |
| 94 | B |
| 95 | A |
| 96 | B |
| 97 | A |
| 98 | A |
| 99 | C |
| 100 | B |

TABLE 19

| Example | PI3Kγ |
|---|---|
| 101 | A |
| 102 | B |
| 103 | B |
| 104 | B |
| 105 | B |
| 106 | A |
| 107 | B |
| 108 | A |
| 109 | B |
| 110 | A |
| 111 | A |
| 112 | A |
| 113 | B |
| 114 | A |
| 115 | B |
| 116 | A |
| 117 | A |
| 118 | A |
| 119 | A |
| 120 | A |
| 121 | A |
| 122 | A |
| 123 | A |
| 124 | A |
| 125 | A |
| 126 | A |
| 127 | A |
| 128 | A |
| 129 | A |
| 130 | A |
| 131 | A |
| 132 | A |
| 133 | A |
| 134 | A |
| 135 | A |
| 136 | A |
| 137 | C |

TABLE 19-continued

| Example | PI3Kγ |
|---|---|
| 138 | A |
| 139 | A |
| 140 | A |
| 141 | A |
| 142 | A |
| 143 | A |
| 144 | A |
| 145 | A |
| 146 | A |
| 147 | A |
| 148 | A |
| 149 | A |
| 150 | A |
| 151 | A |
| 152 | A |
| 153 | A |
| 154 | A |
| 155 | A |
| 156 | A |
| 157 | A |
| 158 | A |
| 159 | A |
| 160 | A |
| 161 | A |
| 162 | A |
| 163 | B |
| 164 | A |
| 165 | A |
| 166 | A |
| 167 | A |
| 168 | B |
| 169 | A |
| 170 | A |
| 171 | A |
| 172 | A |
| 173 | A |
| 174 | A |
| 175 | A |
| 176 | A |

INDUSTRIAL APPLICABILITY

The compound of the present invention has a PI3Kγ inhibitory activity, and can be used as a prophylactic or therapeutic agent for rheumatoid arthritis, Crohn's disease, irritable bowel syndrome, Sjoegren's syndrome, multiple sclerosis, systemic lupus erythematosus, asthma, atopic dermatitis, arteriosclerosis, organ transplant rejection, cancers, retinosis, psoriasis, arthrosis deformans, age-related macular degeneration, type II diabetes mellitus, insulin resistance, obesity, fatty liver (NAFLD), non-alcoholic hepatitis (NASH) or hyperlipidemia.

The invention claimed is:
1. A compound represented by a formula (1)

[Formula 1]

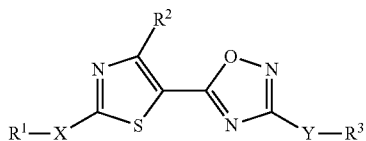

(1)

wherein X represents a formula —$NR^{X1}$—, a formula —$C(O)NR^{X1}$—, a formula —$NR^{X1}C(O)NR^{X2}$—, a formula —$OC(O)NR^{X1}$— or a formula —$SO_2NR^{X1}$—,
wherein $R^{X1}$ and $R^{X2}$ are each independently a hydrogen atom or an alkyl group having 1 to 6 carbon atoms;

$R^1$ represents an alkyl group having 1 to 6 carbon atoms,
wherein the alkyl group may optionally be substituted with 1 to 5 substituents selected from the group consisting of a cycloalkyl group having 3 to 6 carbon atoms, a halogen atom, a cyano group, a hydroxy group, an alkoxy group having 1 to 6 carbon atoms, a formula —$NR^{11}R^{12}$, a formula —$NR^{13}COR^{14}$, a formula —$CO_2R^{15}$, a formula —$CONR^{16}R^{17}$, a formula —$COR^{18}$, a formula —$NR^{19}CONR^{20}R^{21}$, a formula —$SO_2NR^{22}R^{23}$, a formula —$SO_2R^{24}$, a formula —$NR^{25}CO_2R^{26}$, a formula —$OCOR^{27}$ and a 5- or 6-membered heterocyclic group which may optionally be substituted with an alkyl group having 1 to 6 carbon atoms, $R^{11}$, $R^{12}$, $R^{16}$, $R^{17}$, $R^{20}$, $R^{21}$, $R^{22}$ and $R^{23}$ are each independently a hydrogen atom or an alkyl group having 1 to 6 carbon atoms which may optionally be substituted with 1 to 3 substituents selected from a hydroxy group and an alkoxy group having 1 to 6 carbon atoms, or $R^{11}$ and $R^{12}$, $R^{16}$ and $R^{17}$, $R^{20}$ and $R^{21}$, and $R^{22}$ and $R^{23}$, together with the nitrogen atom to which they are bound, may each form a 5- or 6-membered saturated heterocyclic group (wherein the heterocyclic group may optionally be substituted with 1 to 3 substituents selected from the group consisting of a hydroxy group, an alkoxy group having 1 to 6 carbon atoms and an alkoxycarbonyl group having 2 to 7 carbon atoms), and $R^{13}$, $R^{14}$, $R^{15}$, $R^{18}$, $R^{19}$, $R^{24}$, $R^{25}$, $R^{26}$ and $R^{27}$ are each independently a hydrogen atom, or an alkyl group having 1 to 6 carbon atoms which may optionally be substituted with 1 to 3 substituents selected from a hydroxy group and an alkoxy group having 1 to 6 carbon atoms;

$R^2$ represents an alkyl group having 1 to 6 carbon atoms which may optionally be substituted with 1 to 3 halogen atoms;

Y represents a single bond; and
$R^3$ represents a pyridyl group or a pharmaceutically acceptable salt thereof,
with the proviso that when X is a formula —NH—, N,4-dimethyl-5-[3-(pyridin-3-ylmethyl)-1,2,4-oxadiazol-5-yl]-1,3-thiazol-2-amine and N-ethyl-4-methyl-5-[3-(pyridin-2-yl)-1,2,4-oxadiazol-5-yl]-1,3-thiazol-2-amine are excluded.

2. The compound or a pharmaceutically acceptable salt thereof according to claim 1, wherein X represents a formula —$NR^{X1}$—, a formula —$C(O)NR^{X1}$—, a formula —$NR^{X1}C(O)NR^{X}$—, or a formula —$OC(O)NR^{X1}$—,
wherein $R^{X1}$ and $R^{X2}$ are each independently a hydrogen atom or an alkyl group having 1 to 6 carbon atoms;

$R^1$ is an alkyl group having 1 to 6 carbon atoms
wherein the alkyl group may optionally be substituted with 1 to 5 substituents selected from the group consisting of a hydroxy group, an alkoxy group having 1 to 6 carbon atoms, a formula —$NR^{11}R^{12}$, a formula —$NR^{13}COR^{14}$, a formula —$CO_2R^{15}$, a formula —$CONR^{16}R^{17}$, a formula —$SO_2NR^{22}R^{23}$, a formula —$NR^{25}CO_2R^{26}$, a formula —$OCOR^{27}$ and a 5- or 6-membered heterocyclic group which may optionally be substituted with an alkyl group having 1 to 6 carbon atoms, $R^{11}$, $R^{12}$, $R^{16}$, $R^{17}$, $R^{22}$ and $R^{23}$ are each independently a hydrogen atom or an alkyl group having 1 to 6 carbon atoms which may optionally be substituted with 1 to 3 substituents selected from a hydroxy group and an alkoxy group having 1 to 6 carbon atoms, or $R^{16}$ and $R^{17}$, together with the nitrogen atom to which they are bound, may form a 5- or 6-membered saturated heterocyclic group (wherein the heterocyclic group may optionally be substituted with 1 to 3 substituents selected from the group consisting of a hydroxy group, an alkoxy group having 1 to 6 carbon atoms and an alkoxycarbonyl group having 2 to 7 carbon atoms), and $R^{13}$, $R^{14}$, $R^{15}$, $R^{25}$, $R^{26}$ and $R^{27}$ are each independently a hydrogen atom, or an alkyl group having 1 to 6 carbon atoms which may optionally be substituted with a hydroxy group;

$R^2$ is an alkyl group having 1 to 6 carbon atoms;

Y represents a single bond; and $R^3$ is a pyridyl group.

3. The compound or a pharmaceutically acceptable salt thereof according to claim 1, wherein X is a formula —C(O)NH—; and $R^1$ is an alkyl group having 1 to 6 carbon atoms, wherein the alkyl group may optionally be substituted with 1 to 5 substituents selected from the group consisting of a hydroxy group, an alkoxy group having 1 to 6 carbon atoms, a formula —$NR^{11}R^{12}$, a formula —$CO_2R^{15}$, a formula —$CONR^{16}R^{17}$, formula —$SO_2NR^{22}R^{23}$, a formula —$NR^{25}CO_2R^{26}$ and a formula —$OCOR^{27}$, $R^{11}$, $R^{12}$, $R^{16}$, $R^{17}$, $R^{22}$ and $R^{23}$ are each independently a hydrogen atom, or an alkyl group having 1 to 6 carbon atoms which may optionally be substituted with 1 to 3 substituents selected from a hydroxy group and an alkoxy group having 1 to 6 carbon atoms, and $R^{15}$, $R^{25}$, $R^{26}$ and $R^{27}$ are each independently a hydrogen atom, or an alkyl group having 1 to 6 carbon atoms which may optionally be substituted with a hydroxy group.

4. The compound or a pharmaceutically acceptable salt thereof according to claim 1, wherein X is a formula —NHC(O)NH— or a formula —OC(O)NH—.

5. The compound or a pharmaceutically acceptable salt thereof according to claim 1, wherein $R^1$ is an alkyl group having 1 to 6 carbon atoms, the alkyl group may optionally be substituted with 1 to 5 substituents selected from the group consisting of a formula —$CO_2R^{15}$, a formula —$CONR^{16}R^{17}$ and a 5- or 6-membered heterocyclic group which may optionally be substituted with an alkyl group having 1 to 6 carbon atoms, $R^{16}$ and $R^{17}$ are each independently a hydrogen atom or an alkyl group having 1 to 6 carbon atoms which may optionally be substituted with 1 to 3 substituents selected from a hydroxy group and an alkoxy group having 1 to 6 carbon atoms, or $R^{16}$ and $R^{17}$, together with the nitrogen atom to which they are bound, may form a 5- or 6-membered saturated heterocyclic group (wherein the heterocyclic group may optionally be substituted with 1 to 3 substituents selected from the group consisting of a hydroxy group, an alkoxy group having 1 to 6 carbon atoms and an alkoxycarbonyl group having 2 to 7 carbon atoms), and $R^{15}$ represents a hydrogen atom, or an alkyl group having 1 to 6 carbon atoms which may optionally be substituted with a hydroxy group.

6. A pharmaceutical composition comprising a compound or a pharmaceutically acceptable salt thereof according to claim 1, and a pharmaceutically acceptable carrier.

* * * * *